US006913934B2

(12) United States Patent
Dales et al.

(10) Patent No.: US 6,913,934 B2
(45) Date of Patent: Jul. 5, 2005

(54) APPARATUS AND METHODS FOR PARALLEL PROCESSING OF MULTIPLE REACTION MIXTURES

(75) Inventors: G. Cameron Dales, Saratoga, CA (US); Gary Diamond, San Jose, CA (US); Trevor G. Frank, Fremont, CA (US); J. Christopher Freitag, Santa Clara, CA (US); Kenneth S. Higashihara, Mountain View, CA (US); Dave Huffman, Livermore, CA (US); Jonah R. Troth, Mountain View, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 600 days.

(21) Appl. No.: 10/040,988

(22) Filed: Jan. 7, 2002

(65) Prior Publication Data

US 2002/0110493 A1 Aug. 15, 2002

Related U.S. Application Data

(63) Continuation-in-part of application No. 09/772,101, filed on Jan. 26, 2001, now Pat. No. 6,759,014.

(51) Int. Cl.[7] .............................. G01N 1/10; B01L 3/02

(52) U.S. Cl. ...................... 436/180; 436/37; 436/155; 436/159; 422/63; 422/67; 422/100; 422/129; 422/130; 422/131; 73/863.82; 73/863.83; 73/864.01; 73/864.24; 73/864.25; 73/864.31

(58) Field of Search ...................... 73/863.31–863.32, 73/863.82–863.83, 864.01, 864.11, 864.13, 864.15, 864.16, 864.24, 864.25, 864.31, 864.87; 422/63–67, 100, 129–131, 135; 436/37, 155, 159, 180, 183; 604/27, 35–36, 187, 239, 240, 272, 274

(56) References Cited

U.S. PATENT DOCUMENTS

| 2,217,602 | A | * | 10/1940 | Smith | 604/272 |
| 2,409,979 | A | * | 10/1946 | Huber | 604/274 |
| 2,512,568 | A | * | 6/1950 | Saffir | 604/239 |
| 2,634,726 | A | * | 4/1953 | Hanson | 604/274 |
| 2,697,438 | A | * | 12/1954 | Hickey | 604/274 |
| 2,717,599 | A | * | 9/1955 | Huber | 604/274 |
| 2,746,454 | A | * | 5/1956 | Sorensen | 604/272 |
| 2,916,057 | A | * | 12/1959 | Carle et al. | 73/864.16 |
| 2,991,161 | A | | 7/1961 | Gasche | |
| 2,996,363 | A | | 8/1961 | Ruyak | |
| 3,186,408 | A | * | 6/1965 | Jacob | 604/240 |
| 3,390,678 | A | * | 7/1968 | Lewis et al. | 604/240 |
| 3,607,094 | A | | 9/1971 | Beer | |
| 3,739,779 | A | * | 6/1973 | Pfleger | 604/205 |

(Continued)

FOREIGN PATENT DOCUMENTS

| DE | 43 05 405 | 5/1994 |
| EP | 0 371 872 | 6/1990 |
| EP | 0 529 504 A2 | 3/1993 |

(Continued)

OTHER PUBLICATIONS

"Heated Reacto—Stations," Estem Corporation, Oct. 1997.
"Microreactor Technology: Focusing the German Activities in this Novel and Promising Field of Chemical Process Engineering," J.P. Baselt, A. Forster, J. Herrmann, and D. Tiebes, pp. 13–17, 1997.

(Continued)

*Primary Examiner*—Arlen Soderquist
(74) *Attorney, Agent, or Firm*—Senniger Powers

(57) ABSTRACT

A cannula for use in transferring small volumes of fluid materials, such as in a parallel reaction process. The cannula comprises a long thin needle having various end (port) configurations, and an adapter for connecting the needle to a fluid line. The adapter may include the combination of a reservoir and transition, or simply a transition.

12 Claims, 31 Drawing Sheets

U.S. PATENT DOCUMENTS

| | | | | |
|---|---|---|---|---|
| 3,869,068 A | * | 3/1975 | Chen | 73/864.22 |
| 3,924,617 A | * | 12/1975 | Ferro | 604/411 |
| 4,000,976 A | * | 1/1977 | Kramer et al. | 422/65 |
| 4,076,503 A | | 2/1978 | Atwood et al. | |
| 4,195,131 A | | 3/1980 | Papas | |
| 4,325,914 A | | 4/1982 | Ruyak | |
| 4,343,766 A | * | 8/1982 | Sisti et al. | 422/63 |
| 4,347,750 A | | 9/1982 | Tersteeg et al. | |
| 4,393,726 A | | 7/1983 | Tamm et al. | |
| 4,422,151 A | * | 12/1983 | Gilson | 700/283 |
| 4,499,053 A | * | 2/1985 | Jones | 422/68.1 |
| 4,526,046 A | * | 7/1985 | Oberli | 73/864.16 |
| 4,598,049 A | | 7/1986 | Zelinka et al. | |
| 4,640,023 A | | 2/1987 | Mori et al. | |
| 4,671,941 A | | 6/1987 | Niina et al. | |
| 4,736,638 A | * | 4/1988 | Okawa et al. | 73/864.24 |
| 4,746,490 A | | 5/1988 | Saneii | |
| 4,748,002 A | | 5/1988 | Neimark et al. | |
| 4,795,445 A | * | 1/1989 | Jensen | 604/240 |
| 4,842,585 A | * | 6/1989 | Witt | 604/158 |
| 4,865,986 A | | 9/1989 | Coy et al. | |
| 4,907,158 A | * | 3/1990 | Kettler et al. | 700/58 |
| 4,927,603 A | * | 5/1990 | Fischer et al. | 422/67 |
| 4,954,149 A | * | 9/1990 | Fullemann | 96/105 |
| 5,085,832 A | | 2/1992 | Shaw et al. | |
| 5,100,390 A | * | 3/1992 | Lubeck et al. | 604/158 |
| 5,114,854 A | | 5/1992 | Bertholdt | |
| 5,207,658 A | * | 5/1993 | Rosen et al. | 604/272 |
| 5,252,296 A | | 10/1993 | Zuckermann et al. | |
| 5,295,980 A | * | 3/1994 | Ersek | 604/272 |
| 5,324,483 A | | 6/1994 | Cody et al. | |
| 5,380,495 A | | 1/1995 | Chang et al. | |
| 5,395,594 A | | 3/1995 | Nokihara et al. | |
| 5,443,791 A | | 8/1995 | Cathcart et al. | |
| 5,499,193 A | | 3/1996 | Sugawara et al. | |
| 5,503,805 A | | 4/1996 | Sugarman et al. | |
| 5,515,871 A | * | 5/1996 | Bittner et al. | 128/898 |
| 5,538,694 A | | 7/1996 | Delius | |
| 5,593,642 A | | 1/1997 | DeWitt et al. | |
| 5,602,756 A | | 2/1997 | Atwood et al. | |
| 5,609,826 A | | 3/1997 | Cargill et al. | |
| 5,659,874 A | | 8/1997 | Rault et al. | |
| 5,714,127 A | | 2/1998 | DeWitt et al. | |
| 5,716,584 A | | 2/1998 | Baker et al. | |
| 5,746,982 A | | 5/1998 | Saneii et al. | |
| 5,747,708 A | * | 5/1998 | Weiberth | 73/863.81 |
| 5,753,514 A | | 5/1998 | Karlsson et al. | |
| 5,762,881 A | | 6/1998 | Harness et al. | |
| 5,841,959 A | | 11/1998 | Guiremand | |
| 5,866,342 A | | 2/1999 | Antonenko et al. | |
| 5,888,830 A | | 3/1999 | Mohan et al. | |
| 5,961,925 A | | 10/1999 | Ruediger et al. | |
| 5,985,356 A | | 11/1999 | Schultz et al. | |
| 6,030,917 A | | 2/2000 | Weinberg et al. | |
| 6,045,755 A | * | 4/2000 | Lebl et al. | 422/65 |
| 6,086,831 A | | 7/2000 | Harness et al. | |
| 6,120,741 A | | 9/2000 | Jacquault et al. | |
| 6,132,686 A | | 10/2000 | Gallup et al. | |
| 6,306,658 B1 | * | 10/2001 | Turner et al. | 436/37 |
| 6,455,316 B1 | * | 9/2002 | Turner et al. | 436/37 |
| 6,759,014 B2 | * | 7/2004 | Dales et al. | 422/130 |

FOREIGN PATENT DOCUMENTS

| | | |
|---|---|---|
| EP | 0 895 087 | 2/1999 |
| EP | 0 963 791 A2 | 12/1999 |
| FR | 2 630 216 | 10/1989 |
| WO | WO 94/04929 | 3/1994 |
| WO | WO 96 08725 | 3/1996 |
| WO | WO 96/14930 | 5/1996 |
| WO | WO 97/09353 | 3/1997 |
| WO | WO 97 11375 | 3/1997 |
| WO | WO 98/04102 | 1/1998 |
| WO | WO 98/13137 | 4/1998 |
| WO | WO 98 18518 | 5/1998 |
| WO | WO 98/40159 | 9/1998 |
| WO | WO 98/57740 | 12/1998 |
| WO | WO 99/30817 | 6/1999 |
| WO | WO 00/09255 | 2/2000 |

OTHER PUBLICATIONS

MultiReactor™—Reactor Block, sales literature, RoboSynthon, Inc., 6 pages.

Reaction Blocks, price list and sales literature, J–KEM® Scientific, Inc., 2 pages.

World Wide Web argotech.com/quest May 18, 1998 "NAUTILUS 2400" information.

World Wide Web argotech.com/quest May 18, 1998 "QUEST 210" information.

World Wide Web calbay.com Mar. 31, 1998 "Viscoliner" information.

World Wide Web calscorp.com/about_csc Feb. 8, 1999 "About Calorimetry Sciences Corp." information.

World Wide Web mettler.com Aug. 10, 1998 "Automatic Laboratory Reactors, Reaction Calorimeters and On–line Analysis" information.

World Wide Web tecan.ch Jul. 14, 1998 "CAVRO RSP 9000 Robotic Sample Processor" information.

World Wide Web thermometric.com/calorimetry Jul. 27, 1998 "Caloimetry" information.

Abstract of Japanese Patent No. 04047266, Published Feb. 17, 1992, 1 page.

* cited by examiner

FIG. 26
FIG. 27
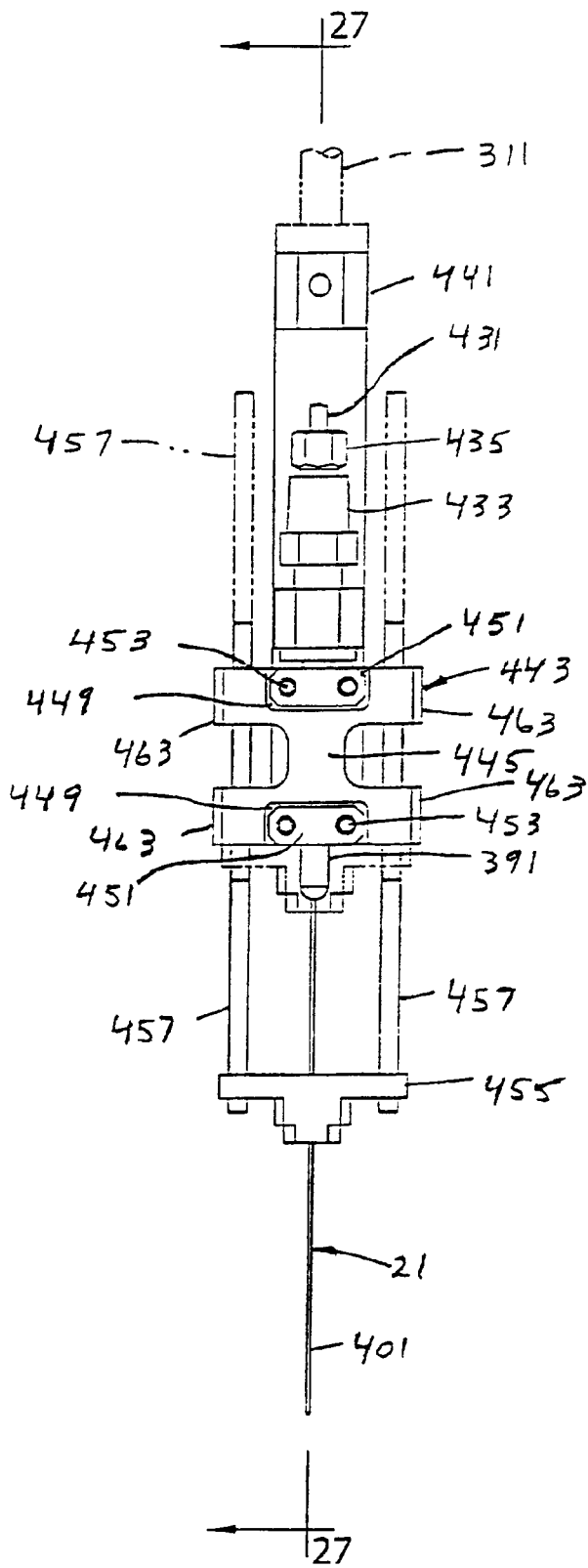
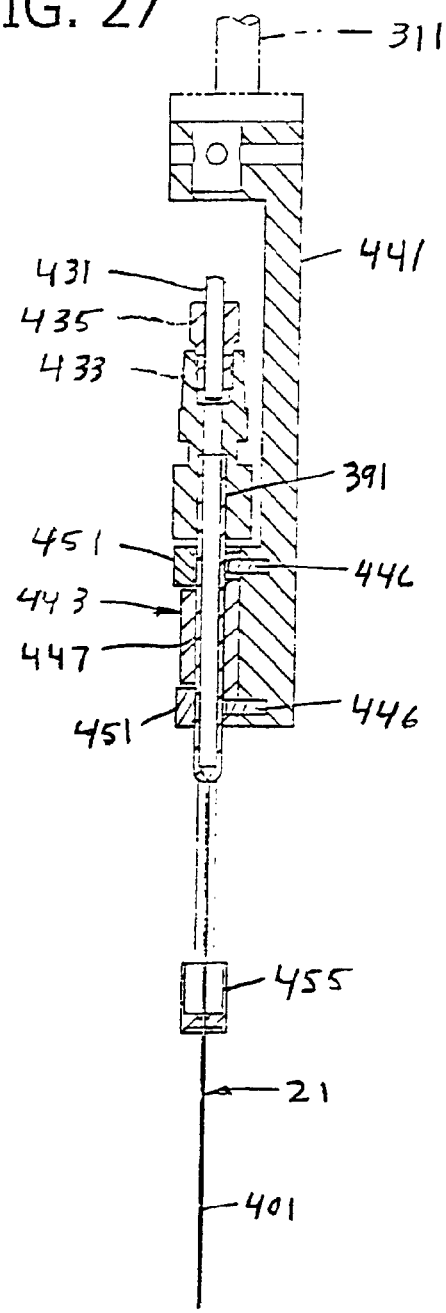

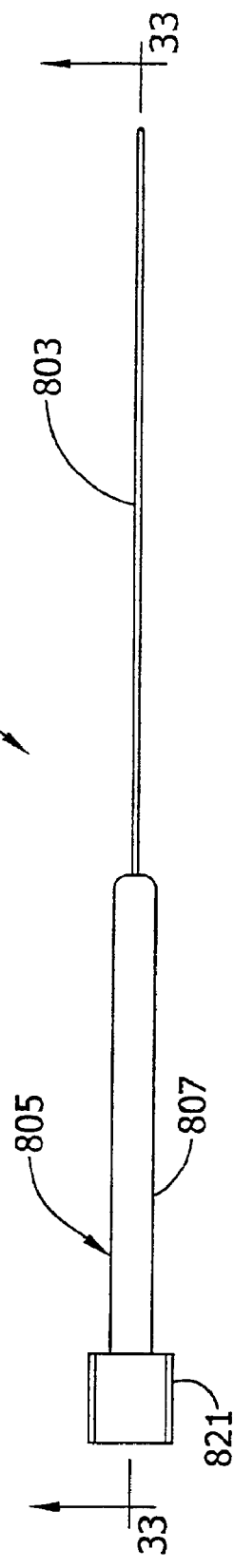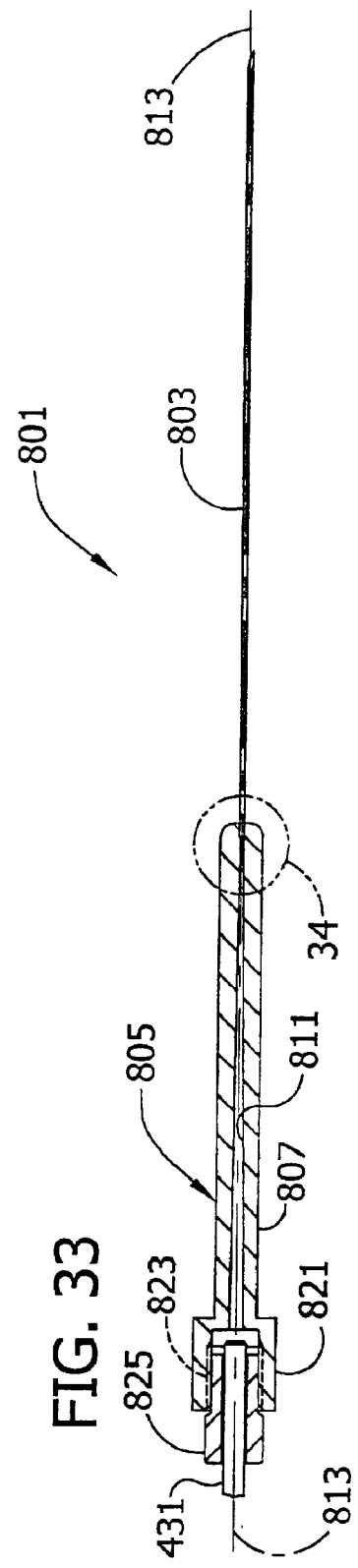

APPARATUS AND METHODS FOR PARALLEL PROCESSING OF MULTIPLE REACTION MIXTURES

CROSS REFERENCE TO RELATED APPLICATIONS

The invention of the present application is a continuation-in-part of U.S. patent application Ser. No. 09/772,101, filed on Jan. 26, 2001, entitled Apparatus and Methods for Parallel Processing of Multiple Reaction Mixtures, now issued as U.S. Pat. No. 6,759,014, the entire disclosure of which is incorporated herein by reference.

BACKGROUND OF THE INVENTION

The present invention relates generally to parallel reactors, and in particular, to parallel research reactors suitable for use in a combinatorial (i.e., high-throughput) science research program in which chemical reactions are conducted simultaneously using small volumes of reaction materials to efficiently and economically screen large libraries of chemical materials.

The present invention is related to co-owned International Application No. PCT/US 99/18358, filed Aug. 12, 1999 by Turner et al., entitled Parallel Reactor with Internal Sensing and Method of Using Same, published Feb. 24, 2000 (International Publication No. WO 00/09255), and which is incorporated herein by reference for all purposes. This PCT application claims priority from the following co-owned, co-pending U.S. applications bearing the same title, all of which are also incorporated by reference: Ser. No. 09/211,982, filed Dec. 14, 1998 by Turner et al. (issued Oct. 23, 2001, as U.S. Pat. No. 6,306,658) and Ser. No. 09/177,170, filed Oct. 22, 1998 by Dales et al., claiming the benefit of provisional application Ser. No. 60/096,603, filed Aug. 13, 1998 by Dales et al. The present invention is also related to co-owned, co-pending U.S. application Ser. No. 09/548,848, filed Apr. 13, 2000 by Turner et al., entitled Parallel Reactor with Internal Sensing and Method of Using Same, claiming priority from the aforementioned PCT application; U.S. application Ser. No. 09/239,223, filed Jan. 29, 1999 by Wang et al., entitled Analysis and Control of Parallel Chemical Reactions; U.S. application Ser. No. 09/873,176, filed Jun. 1, 2001, by Nielsen et al., entitled Parallel Semicontinuous or Continuous Reactors, claiming the benefit of U.S. provisional application Ser. No. 60/209,142, filed Jun. 3, 2000, by Nielsen et al., entitled Parallel Semicontinuous or Continuous Stirred Reactors and U.S. Provisional application Ser. No. 60/255,716, filed Dec. 14, 2000, by Nielsen et al., entitled Parallel Semicontinuous or Continuous Stirred Reactors, all of which are hereby incorporated by reference for all purposes. These applications disclose a number of embodiments for parallel research reactors suitable for use, for example, in combinatorial chemistry applications such as polymer research and catalyst research. However, these embodiments are not especially suited for processing certain slurry materials, such as those containing small particle solids (e.g., silica or alumina particles used as catalyst supports) which can cause excessive wear and/or impede proper operation of reactor equipment, or slurries having aggressive bonding characteristics, which may make them difficult to handle and to clean from reactor equipment. There is a need, therefore, for a system capable of handling such materials.

The present invention is also generally related to systems for effecting the transfer of fluid materials, including slurry materials and solutions, to and from the reactor vessels of a parallel reactor system. Such fluid transfer systems include robotic fluid transfer systems of the type comprising a cannula for holding fluid material, and a robot system for transporting the cannula to a fluid transfer location.

SUMMARY OF THE INVENTION

In view of the foregoing, the objectives of this invention include the provision of a parallel reactor and related methods which overcome deficiencies of known parallel reactors, especially parallel research reactors and methods; the provision of such a parallel reactor and methods which allow for the efficient handling of slurry reactant materials, including slurries containing small particles of solid material, such as silica, and slurries which are especially "sticky" and thus difficult to handle; the provision of such a reactor and methods which provide for the delivery of precise quantities of reactant products, including slurries, to the reaction vessels of a parallel reactor; the provision of such a reactor and methods which provide for the delivery of slurry and other reaction materials under pressure and/or temperature to one or more reaction chambers of the reactor; the provision of an improved cannula for effecting the efficient transfer of fluid materials, such as in a parallel reaction process; the provision of a such cannula which provides for the smooth, substantially laminar flow of fluid through the cannula; the provision of such a cannula which, in certain embodiments, is configured for reducing wear on the seals of a pressure reactor during transfer of materials to and from the reactor; and the provision of a robotic fluid transfer system and related methodology for efficiently effecting the transfer of fluids, including but not limited to slurry materials.

In general, apparatus of the present invention is operable for processing multiple reaction mixtures in parallel. In one aspect, the apparatus comprises a reactor having an exterior surface, and vessels in the reactor for holding the reaction mixtures, each vessel having a central longitudinal axis. A cannula is used for introducing fluid reaction material into the vessels. The cannula has a longitudinal axis, a distal end, and a port generally adjacent said distal end for delivery of reaction material from the cannula. Cannula passages in the reactor extend between the exterior surface of the reactor and the vessels. Each passage extends at an angle relative to the central longitudinal axis of a respective vessel. A robot system is operable to insert the cannula through a selected cannula passage and into a respective vessel for the delivery of the reaction material from the cannula to the respective vessel, and to withdraw the cannula from the selected cannula passage and respective vessel.

Another aspect of the present invention involves a method of loading fluid reaction material into a series of vessels in a reactor, each vessel having a central longitudinal axis. The method comprises, in sequence, (1) inserting a cannula through a cannula passage in the reactor to a position in which the cannula extends at an angle relative to the central longitudinal axis of a first vessel of the series of vessels, and in which a distal end of the cannula is disposed in the vessel, (2) delivering a fluid reaction material from the cannula into the vessel, (3) withdrawing the cannula from said passage, and repeating 1–3 for a second vessel.

The present invention is also directed to a cannula for use in the transfer of small volumes of fluid materials, such as in a parallel reaction process. The cannula comprises a reservoir having a longitudinal axis, an inside dimension defining an interior for containing said fluid materials, an outside dimension, a proximal end and a distal end. The reservoir has a capacity in the range of 10–5000 microliters. The cannula also includes a long thin needle substantially coaxial with the reservoir. The needle has an outside dimension substantially less than the outside dimension of the reservoir and an inside surface defining a flow passage through the needle. The needle further has a proximal end, a distal end, and a port adjacent the distal end for the transfer of fluid materials to and from the needle. A transition joins the proximal end of the needle to the distal end of the reservoir so that the interior of the reservoir is in fluid communication with the flow passage of the needle.

In another aspect of this invention, a cannula comprises a long thin needle having an inside surface defining a flow passage through the needle, a proximal end, a distal end, and a port adjacent the distal end directed at an oblique angle relative to a longitudinal axis of the needle for the transfer of fluid materials to and from the needle. The cannula also includes an adapter for connecting the needle to a fluid line. The adapter has a distal end connected to the proximal end of the needle, a proximal end for connection to the fluid line, and an interior for directing the transfer of fluid between the fluid line and the flow passage of the needle.

The present invention is also directed to a cannula comprising a long thin needle having a longitudinal axis, an inside surface defining a flow passage through the needle, a proximal end, a distal end, and a port adjacent but spaced from the distal end and directed laterally away from the longitudinal axis for the transfer of said fluid materials to and from the needle. The cannula further comprises an adapter for connecting the needle to a fluid line. The adapter has a distal end connected to the proximal end of the needle, a proximal end for connection to the fluid line, and an interior for directing the transfer of fluid between the fluid line and the flow passage of the needle. The distal end of the needle has a smooth, rounded exterior end surface substantially free of exposed sharp edges. As a result, the distal end of the needle may be used to penetrate a seal with only minimal wear on the seal.

In still another aspect of this invention, the cannula comprises a long thin needle having a longitudinal axis, an inside surface defining a flow passage through the needle, a proximal end, a distal end, and a port spaced from the distal end and directed laterally away from the longitudinal axis of the needle for the transfer of fluid materials to and from the needle. The cannula also includes an adapter comprising a transition connecting the needle to a fluid line. The transition has a distal end connected to the proximal end of the needle, a proximal end adapted for connection to the fluid line, and a flow passage in the transition tapered toward the distal end of the transition.

In yet another aspect, the present invention involves a method of preparing and delivering a slurry reaction material into a series of vessels in a reactor. The method comprises (1) mixing a particulate solid material and a liquid to form a substantially homogeneous first slurry in which the particulate solid material is suspended in the liquid, (2) aspirating the first slurry into a cannula carried by a robot system while the slurry is substantially homogeneous, (3) operating the robot system to insert the cannula into the reactor, (4) delivering the slurry from the cannula into the vessel while the cannula is in said cannula passage, and (5) repeating 2–4 for a second vessel and optionally a second slurry.

The present invention is also directed to a robotic fluid transfer system comprising a cannula sized for holding 10 μl–5000 μl of a fluid material, and a robot system for transporting the cannula to a fluid transfer location. The robot system is operable to move the cannula along a first x axis, a second y axis, and a third z axis, and also for rotating the cannula to vary the angular orientation of the cannula.

In another respect, a robotic fluid transfer system of this invention comprises a cannula adapted for containing fluid, and a robot system for transporting the cannula to a fluid transfer location, the robot system being operable to move the cannula along a first axis x, a second axis y, and a third axis z, and also for rotating the cannula to vary the angular orientation of the cannula. A cannula passage is provided at the fluid transfer location for receiving the cannula to effect the transfer of fluid. A fluid transfer system effects fluid transfer while the cannula is in the cannula passage, and a sealing mechanism in the cannula passage seals against leakage of fluid from the passage during the fluid transfer.

The present invention also involves a method of transferring fluids using a cannula. The method comprises connecting the cannula to a robot transport system, and operating the robot transport system to transport the cannula to a fluid transfer location. The transport involves moving the cannula along x, y and z axes, rotating the cannula to an angular orientation off vertical, and inserting the cannula while in said angled orientation into an angled cannula passage. The transfer of fluid is effected while the cannula is in said angled cannula passage.

Other objects and features will be in part apparent and in part pointed out hereinafter.

BRIEF DESCRIPTION OF THE DRAWINGS

FIG. 26 is a front elevation of a mount for mounting the cannula on the robot system, and a support for supporting a needle of the cannula;

FIG. 27 is a vertical section taken on lines 27—27 of FIG. 26;

FIG. 32 is a side elevation of a cannula of alternative construction, comprising a needle and an adapter for connecting the needle to a fluid line (not shown);

FIG. 33 is a sectional view of the cannula of FIG. 32, showing the fluid line;

Corresponding parts are designated by corresponding references numbers throughout the drawings.

DESCRIPTION OF PREFERRED EMBODIMENTS

Figure 1:
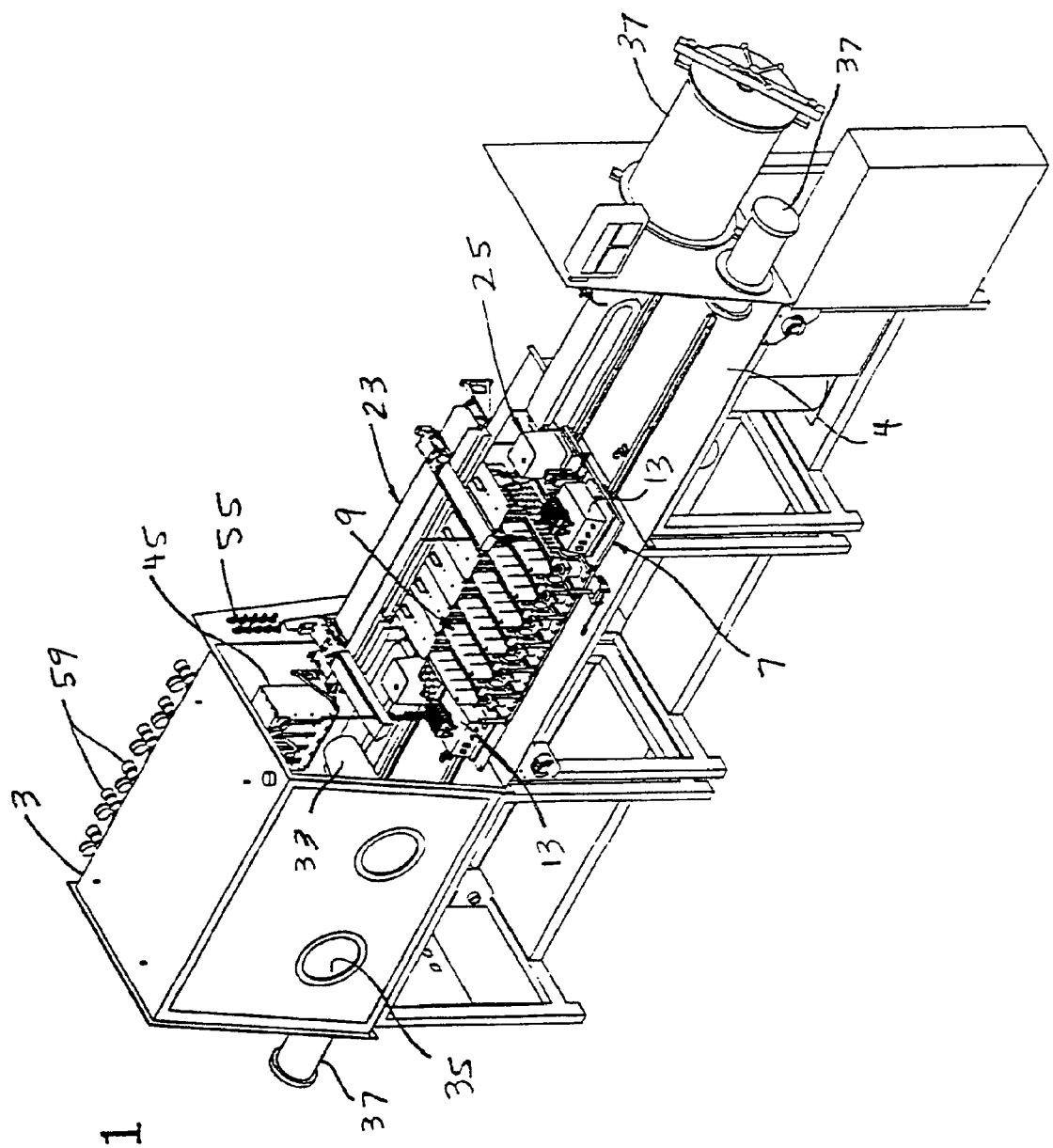
FIG. 1 is a perspective of a parallel reactor of the present invention.

Referring now to the drawings, and more particularly to FIG. 1, apparatus for parallel processing of multiple reaction mixtures is indicated in its entirety by the reference numeral 1. (As used herein, the term "parallel" means that two or more of the multiple reaction mixtures are processed either simultaneously or at least during overlapping time periods.) The apparatus 1, which may be referred to as a parallel reactor system, is similar in certain respects to the parallel reactor system described in the aforementioned publications and applications, including International Application No. PCT/US 99/18358 (International Publication No. WO 00/09255).

Figure 2:
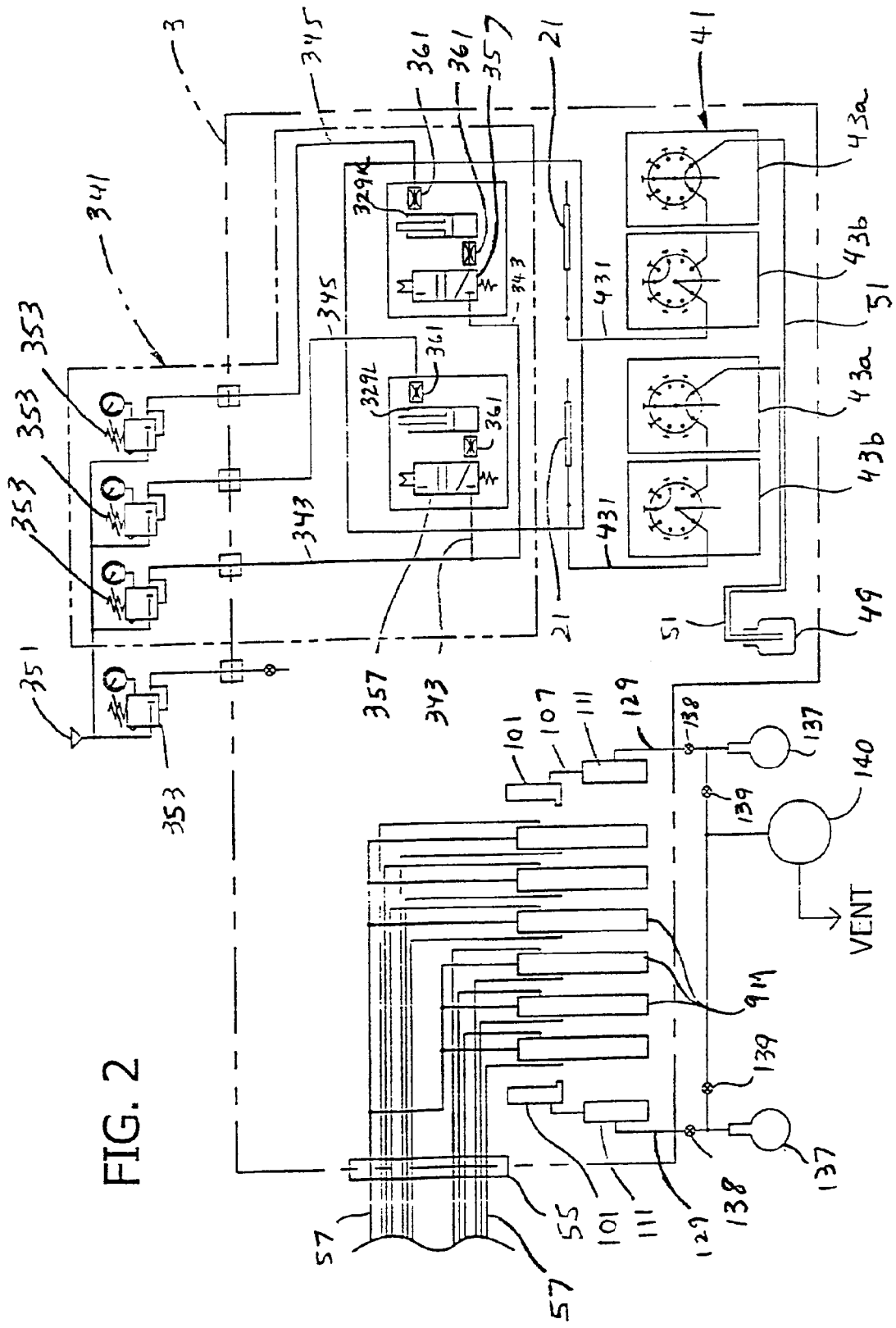
FIG. 2 is a schematic diagram showing key components of the reactor for delivering a slurry fluid to a number of reactor modules.
Figure 3:
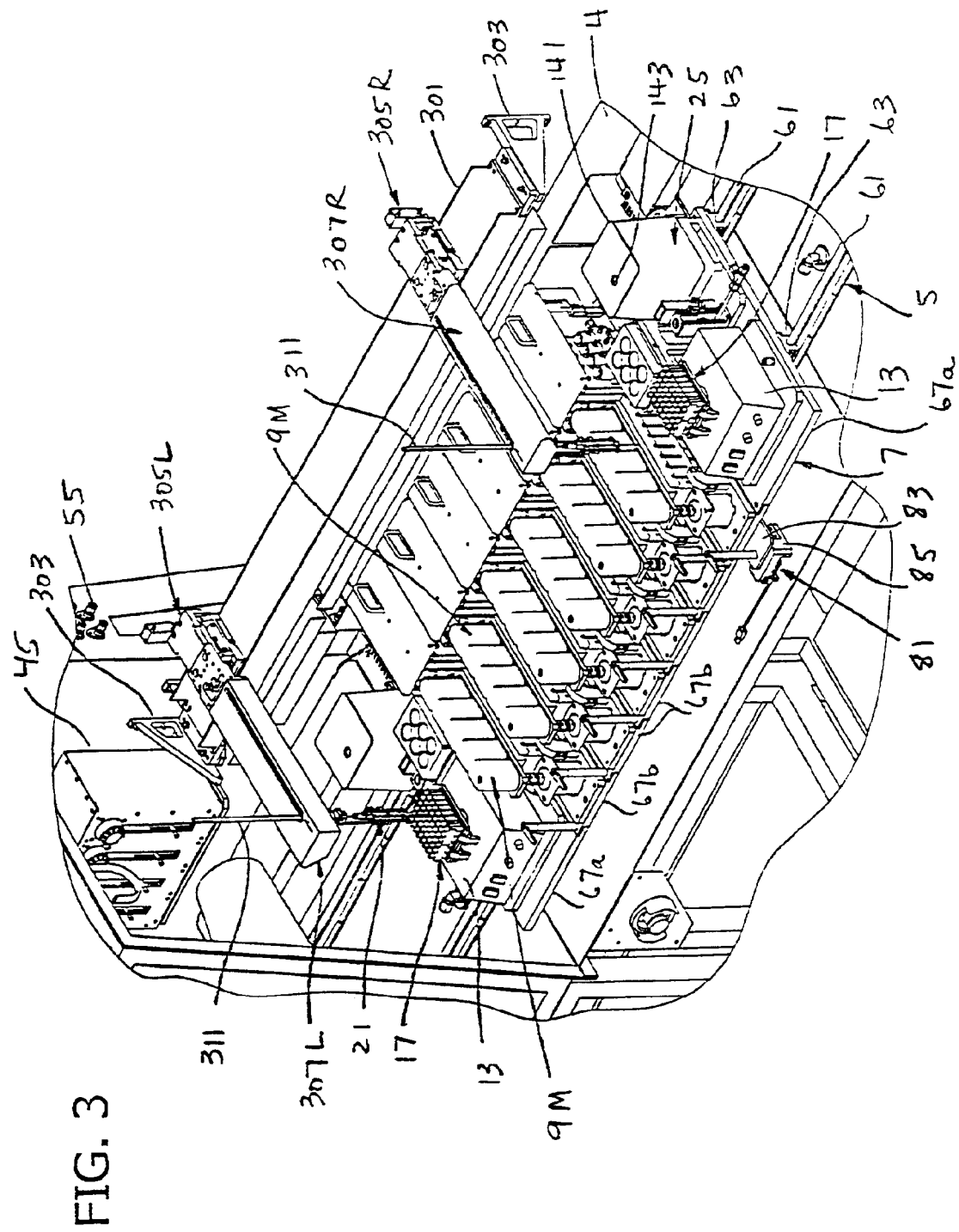
FIG. 3 is an enlarged portion of FIG. 1 showing, among other things, a modular reactor and a robot system for servicing the reactor.
Figure 4:
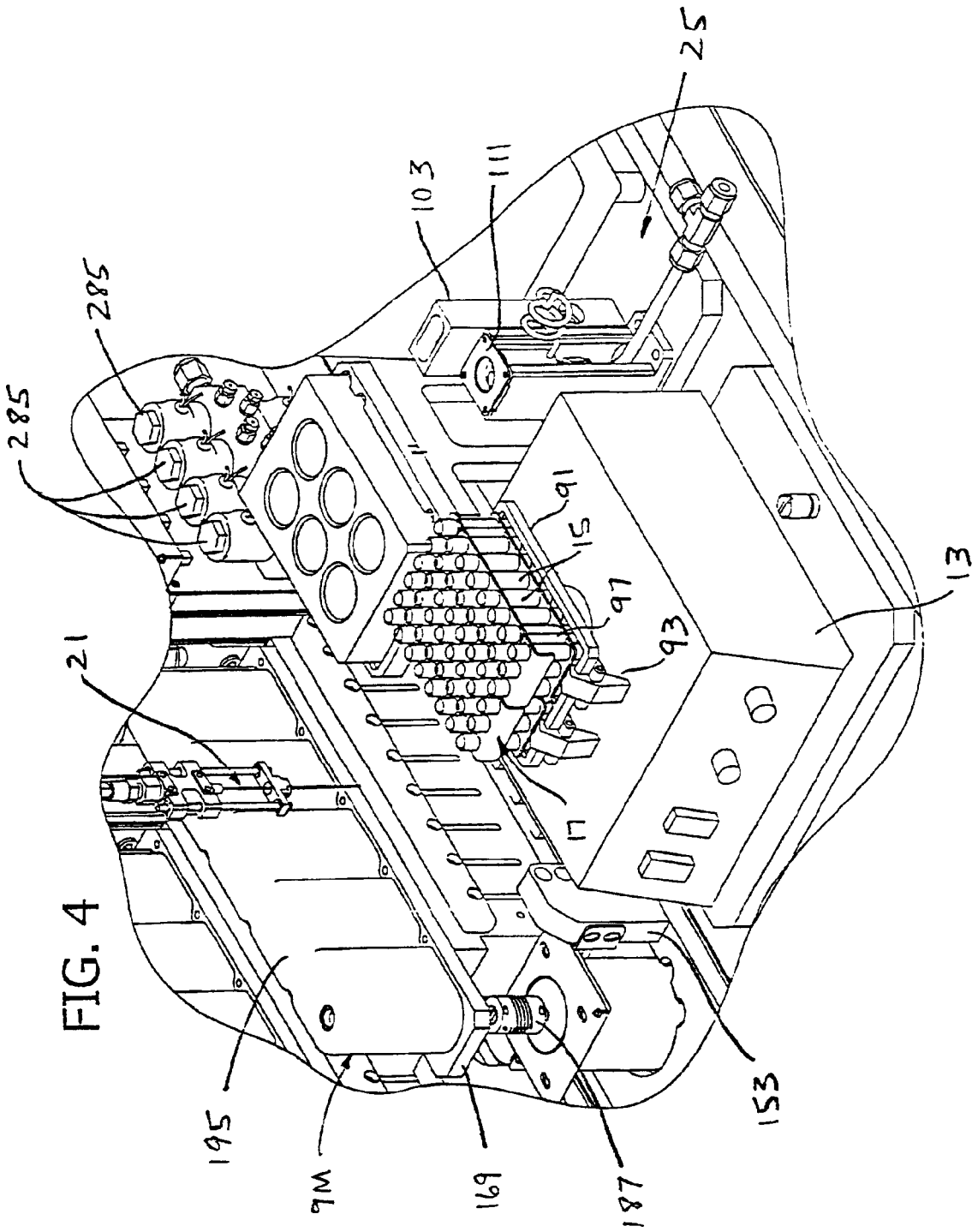
FIG. 4 is an enlarged portion of FIG. 3 showing a shaker and hot and ambient wash towers.

In general, the apparatus 1 comprises an enclosure 3 having a floor 4, a rail system generally designated 5 on the floor 4, and a carriage generally designated 7 slidable on the rail system. A modular reactor 9 comprising a number of reactor modules, each generally designated 9M, are mounted side-by-side on the carriage. Six such reactor modules 9M are shown in FIGS. 1–3, but this number may vary from one to six or more. Further, the reactor need not be modular, but rather it could be a single monolithic reactor. The reactor 9 is preferably a research reactor, but could also be a relatively small-volume production reactor. Two orbital shakers 13 are provided on the carriage 7 for shaking fluid reactants or other reaction materials in mixing vials 15 held by racks 17 mounted on the shakers (FIG. 4). The reaction materials may be in slurry form comprising solid particles, such as silica or alumina particles supporting a catalyst, suspended in a carrier fluid. The apparatus 1 further includes a pair of cannulas, each generally designated 21, and a four-axis robot system, generally indicated at 23, for moving the cannulas to aspirate fluid reaction materials from the vials into the cannulas, and then to move the cannulas into position for delivery of the fluid materials to the reactor modules 9M, as will be described. Alternatively, a single cannula or more than two cannulas could be used to service the reactor modules. Apparatus, generally designated 25, for cleaning the cannulas is also provided on the carriage adjacent each orbital shaker.

In the preferred embodiment, the robot system 23, carriage 7, rail system 5 and various components on the carriage are all enclosed by the enclosure 3, which is a tubular enclosure supported by legs. (For convenience of illustrating the equipment inside the enclosure, certain portions of the top and side walls of the enclosure are omitted in FIG. 1.) The enclosure is preferably what is referred to as a "dry box" or a "glove box" having gloves 33 affixed to the periphery of openings 35 in the side walls of the enclosure to allow an operator to manipulate items inside the enclosure and reduce possible contamination. The enclosure 3 can be gas-tight or filled with a pressurized inert gas (e.g., argon or nitrogen). In either case, the environment is controlled to eliminate contaminants or other material which might interfere with the parallel reaction processes being conducted in the enclosure. Conventional antechambers (air locks) 37 on the enclosure provide access to the interior of the enclosure. Glove box enclosures suitable for use in the present invention are available from, among others, Vacuum Atmospheres Company of Hawthorne, Calif., and M. Braun Inc. of Newburyport, Mass. Other types of enclosures may also be used, such as a purge box which is movable between a non-enclosing position and an enclosing position and purged of contaminants with a pressurized inert gas.

Also disposed within the enclosure 3 is suitable pumping equipment 41 for servicing the two cannulas 21, as schematically shown in FIG. 2. This equipment is of conventional design and may comprise, for example, positive displacement pumps, preferably adapted for small volume increments. Exemplary pumps include four syringe pumps 43 in a housing 45, each syringe pump comprising a pump and associated syringe. In this embodiment, one set of two syringe pumps 43 services one cannula 21 and the other set of two syringe pumps 43 services the other cannula 21. Preferably, one syringe pump 43a of each two-pump set is operable to pump a larger (but still relatively small) volume of fluid, e.g., 5 ml to 25 ml, and the other syringe pump 43b of the two-pump set is operable to pump a smaller volume, e.g., 100 $\mu$l to 1 ml. The amount of fluid pumped for any given reaction preferably will vary from about 5 $\mu$l to about 500 ml, more preferably from about 1 ml to about 500 ml, still more preferably from about 1 ml to about 100 ml, yet more preferably from about 2 ml to about 50 ml, still more preferably from about 2 ml to about 25 ml, and most preferably from about 5 ml to about 15 ml. The two pumps of each two-pump set are connected to a supply 49 of working fluid (e.g., solvent) by a flow line 51. The construction and operation of the syringe pumps 43 is conventional, such pumps being commercially available from Cavro Scientific Instruments of Sunnyvale, Calif., pump part No. 730367 and syringe part No. 730320. Accordingly, a detailed description of these syringe pumps is unnecessary. Suffice it to say that they are operable in two modes, the first being an intake mode to aspirate measured quantities of fluid reaction material into the cannulas 21, and the second being an output mode to pump measured volumes of working fluid to the cannulas 21 to force corresponding volumes of reaction material from the cannulas for delivery to the reactors 9M. Generally speaking, the smaller volume syringe pump 43b is used to pump smaller volumes of fluid, and the larger volume syringe pump 43a is used to pump larger volumes of process material. In the event fluid must be supplied under pressure to a reactor module 9M, the smaller volume syringe pump 43b is preferably used, since it is operable to supply fluids at pressures up to 500 psig. or more.

The enclosure 3 is provided with fittings 55 for attachment of lines 57 which service the reactor modules. These lines 57 are typically used for the delivery of process gases (e.g., reactant and quenching gases) to the reactor modules 9M, as needed, and also to vent the modules, as will be described hereinafter. The gas lines 57 communicate with suitable sources of gas (not shown) under pressure. The pressure of the gas in the lines 57 is controlled by regulators indicated at 59 in FIG. 1.

Referring to FIG. 3, the rail system 5 comprises a pair of guide rails 61 (e.g., linear guide rails of the type available from Thomson Industries, Port Washington, N.Y.) mounted on the table. Slide bushings 63 mounted on the underside of the carriage allow the carriage 7 to slide back and forth on the rails.

The carriage 7 itself (FIGS. 3 and 5) comprises a plurality of interconnected carriage plates 67, including two end plates 67a carrying the orbital shakers 13, cleaning apparatus 25 and other components, and a plurality of intermediate plates 67b, each of which carries a single reactor module 9M. Adjacent carriage plates 67 are connected by rabbet joints 71 comprising overlapping recessed edge margins releasably secured in precise position relative to one another by quick-connect/disconnect devices 75, each of which extends down through aligned holes in the plates. The device may comprise, for example, a vertical shaft 77 having one or more detents (not shown) at its lower end spring-biased to an extended position for reception in corresponding recesses in the lower of the two overlapping edge margins (see FIG. 5), and a manually-operated button 79 at the upper end of the shaft for retracting the detents to allow the shaft to be withdrawn from the holes to disconnect the two carriage plates 67. Upon disconnection, the carriage plates 67 can be moved together as a unit or relative to one another on the rails 61 to facilitate maintenance and repair of the equipment on the carriage as well as to vary the number of carriage plates and reactor modules in the reactor matrix. The carriage 7 is held in a fixed, predetermined home position on the floor 4 by a "master" interlock 81 (similar to the quick connect/disconnect devices) connecting a rigid extension 83 projecting from the carriage to a stationary fixture 85 affixed to the floor (FIG. 3). In the preferred embodiment, disconnection of the "master" interlock 81 to disconnect the carriage 7 from the fixture 85 triggers a shut-off switch which prevents operation of the robot system 23 until the interlock is reinstalled to reconnect the carriage extension 83 to the fixture 85 at the home position. Such reconnection requires precise alignment of holes in the extension and the fixture, which in turn requires that all carriage plates 67 be properly connected and positioned relative to one another. Thus, the robot system 23 cannot be operated until the carriage plates 67 (and all of the components fixedly attached thereon) are precisely located on the floor 4.

As shown in FIG. 4, each vial rack 17 is releasably held in a frame 91 mounted in fixed position on its respective shaker 13. Spring clamps, quick-acting detents 93 or other connectors on the frame 91 may be used for this purpose. The fit between the rack 17 and the frame 91 is a relatively close, tight fit so that the position of each vial in the rack is set for purposes of the computer controlled robot system 23. The rack 17 itself is modular in design, comprising a plurality of horizontal panels 95 held in vertically spaced relation by spacers 97 fastened to the panels. The panels have vertically aligned openings 99 therein for receiving and holding the vials. The modular nature of the construction facilitates different rack configurations, all of which can fit in the same frame 91. For example, the configuration of the rack can be readily changed to accommodate vials of different sizes, or different numbers of vials, or vials arranged in different arrays. Also, the use of relatively thin panels 95 (which may be stamped metal parts) and spacers reduces the weight of the assembly.

Referring again to FIG. 4, the cleaning apparatus 25 comprises a conventional wash tower 101 having a cavity or well 103 therein for receiving a cannula 21 to be washed and rinsed. Suitable cleaning solution (e.g., solvent) at ambient temperature is pumped through the cannula to flush its interior surfaces. Solution exiting the cannula 21 is directed by the walls of the cavity up along the outside of the cannula to clean its exterior surfaces. Waste solution is directed to a drain 107 for disposal (FIG. 2). A wash tower 101 suitable for use in the system is available from Cavro Scientific Instruments of Sunnyvale, Calif., Model No. 727545.

Figure 6:
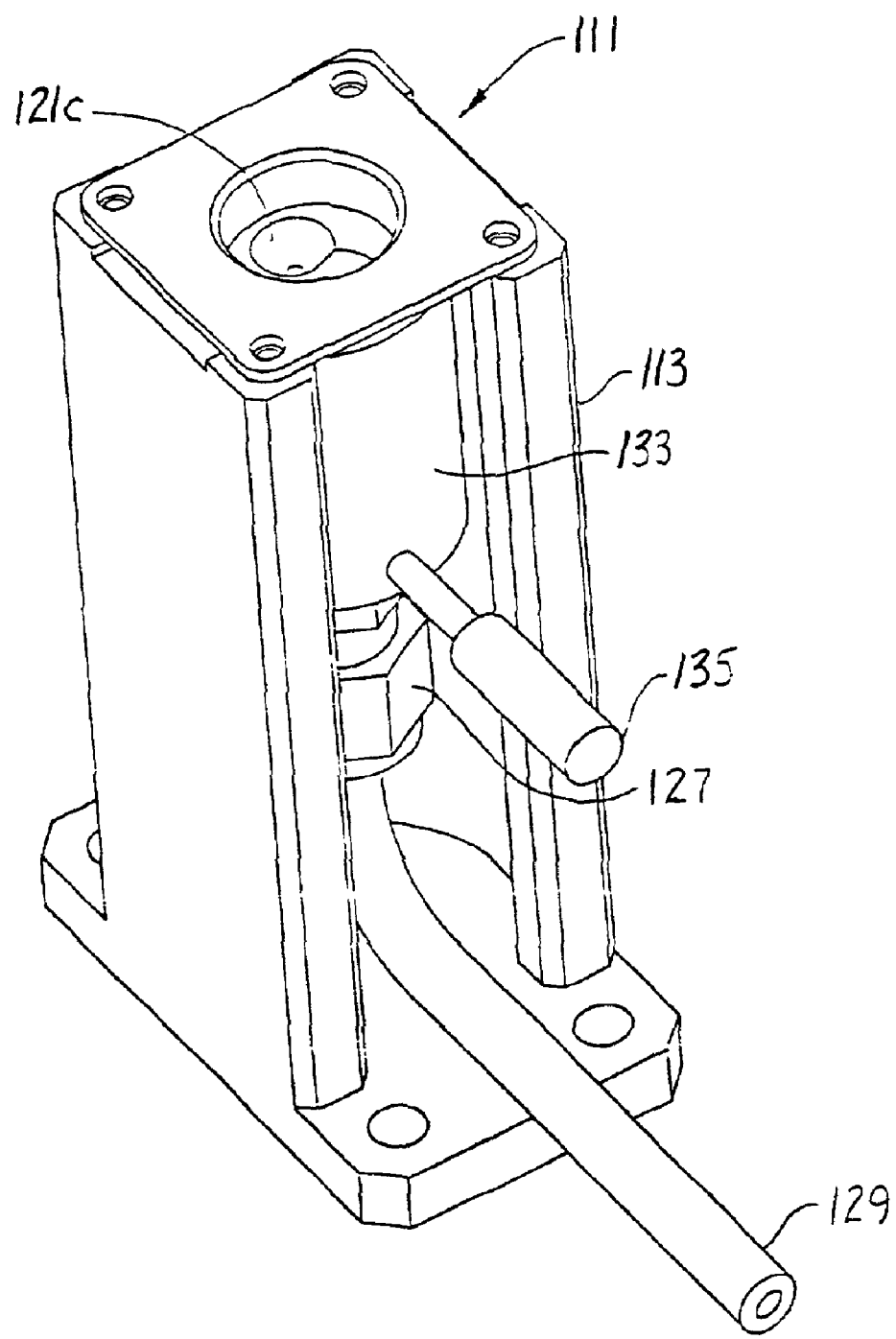
FIG. 6 is a perspective of a heated wash tower of the present invention.
Figure 7:
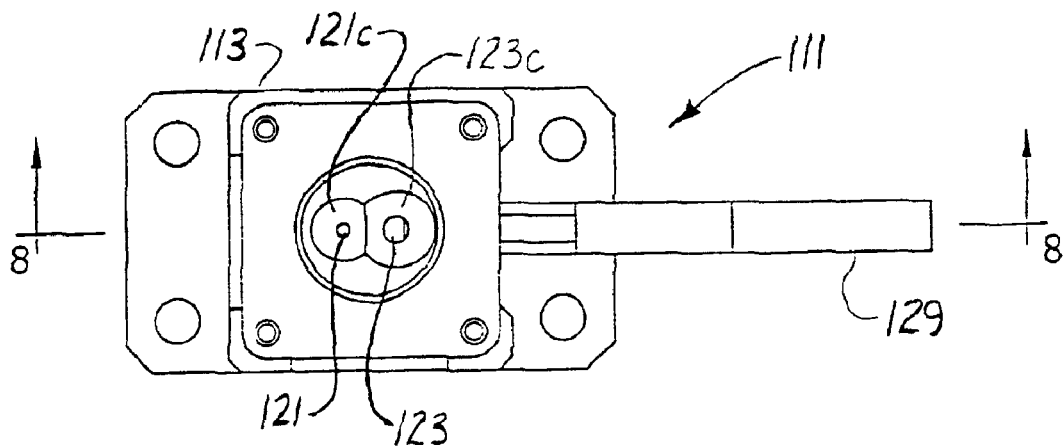
FIG. 7 is a top view of the heated wash tower.
Figure 8:
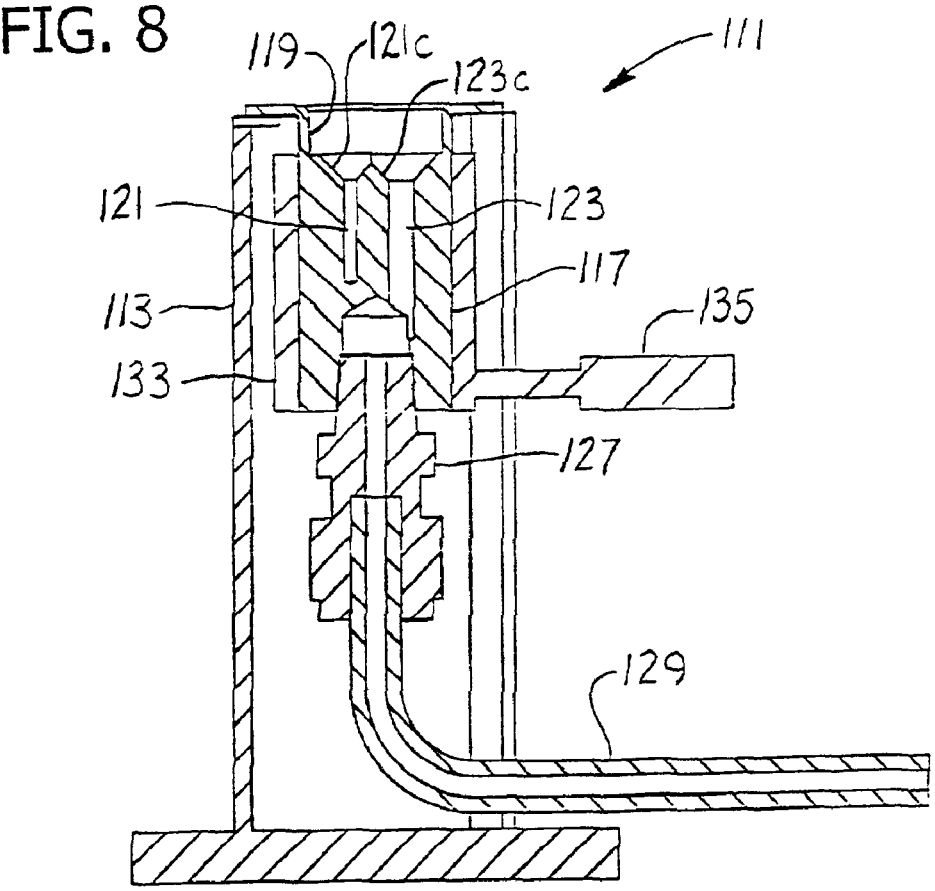
FIG. 8 is a vertical section on lines 8—8 of FIG. 7.

In the event there is a need for more aggressive washing of a cannula, as when slurry reaction materials containing small particulate solids (e.g., solution phase supported catalysts) that tend to adhere to process equipment are being used, the cleaning apparatus 25 may include an ultrasonic bath (not shown) and/or a separate heated wash tower generally indicated at 111. The construction of the heated wash tower is illustrated in FIGS. 6–8. As shown, the tower 111 comprises an upright generally channel-shaped housing 113 on a base 115 secured to an end carriage plate 67a, and a cylindric block 117 of metal supported within the housing having a flanged and recessed upper end 119 and two bores 121, 123 extending down into the block 117 from the recessed upper end 119. The first bore 121 forms a washing well and is relatively narrow in diameter, being only slightly larger in diameter (e.g., 0.035 in. larger) than the outside diameter of the needle of a cannula 21 to be washed. The second bore 123 is larger in diameter and functions as a drain. Intersecting countersinks 121a, 123a at the upper ends of the two bores 121, 123 provide for overflow of wash solution from the washing well 121 into the drain bore 123, the lower end of which is connected via a fitting 127 (e.g., a SWAGELOK® fitting). The cylindric block 117 of the wash tower 101 is surrounded by a jacket 133 containing resistance heating coils (not shown) connected to a source of electric power by a connection 135. The heating coils transfer heat to the cylindric block 117 to heat the block and wash solution in the washing well 121, as will be described later. The solution should be heated to a suitable temperature (e.g., about 170°–200° C.), such as temperature sufficient to remove any coagulated reaction materials on the needle of the cannula 21. As shown in FIG. 2, the drain lines 107, 129 from the wash towers 101, 111 are connected to a suitable drain system including flasks 137 for collecting waste. Valves 138 in the waste lines can be closed to permit disconnection and emptying of the flasks 137. After reconnection of the flasks, valves 139 are opened to permit evacuation of any remaining vapor in the flasks by a means of a vacuum pump 140, following which valves 139 are closed and valves 138 opened to reestablish fluid communication between the flasks and their respective cleaning towers 101, 111 without contaminating the inert environment within the enclosure 3.

In the preferred embodiment, the cleaning apparatus 25 also includes an ultrasonic device 141 (FIG. 3) having a central recess 143 for receiving a cannula 21. This device generates ultrasonic waves which mechanically vibrate the cannula as it is flushed with solvent to provide an additional mechanism, if needed, for removing slurry particles on the interior and exterior surfaces of the needle of the cannula. The ultrasonic device 141 can be used alone or in combination with one of the wash towers 101, 111. A suitable ultrasonic device 141 is manufactured by Branson Ultrasonics Corporation of Danbury, Conn., part number B3-R, and distributed by Cole-Parmer Instrument Company of Vernon Hills, Ill., under part number P-08849-00.

Figure 9:
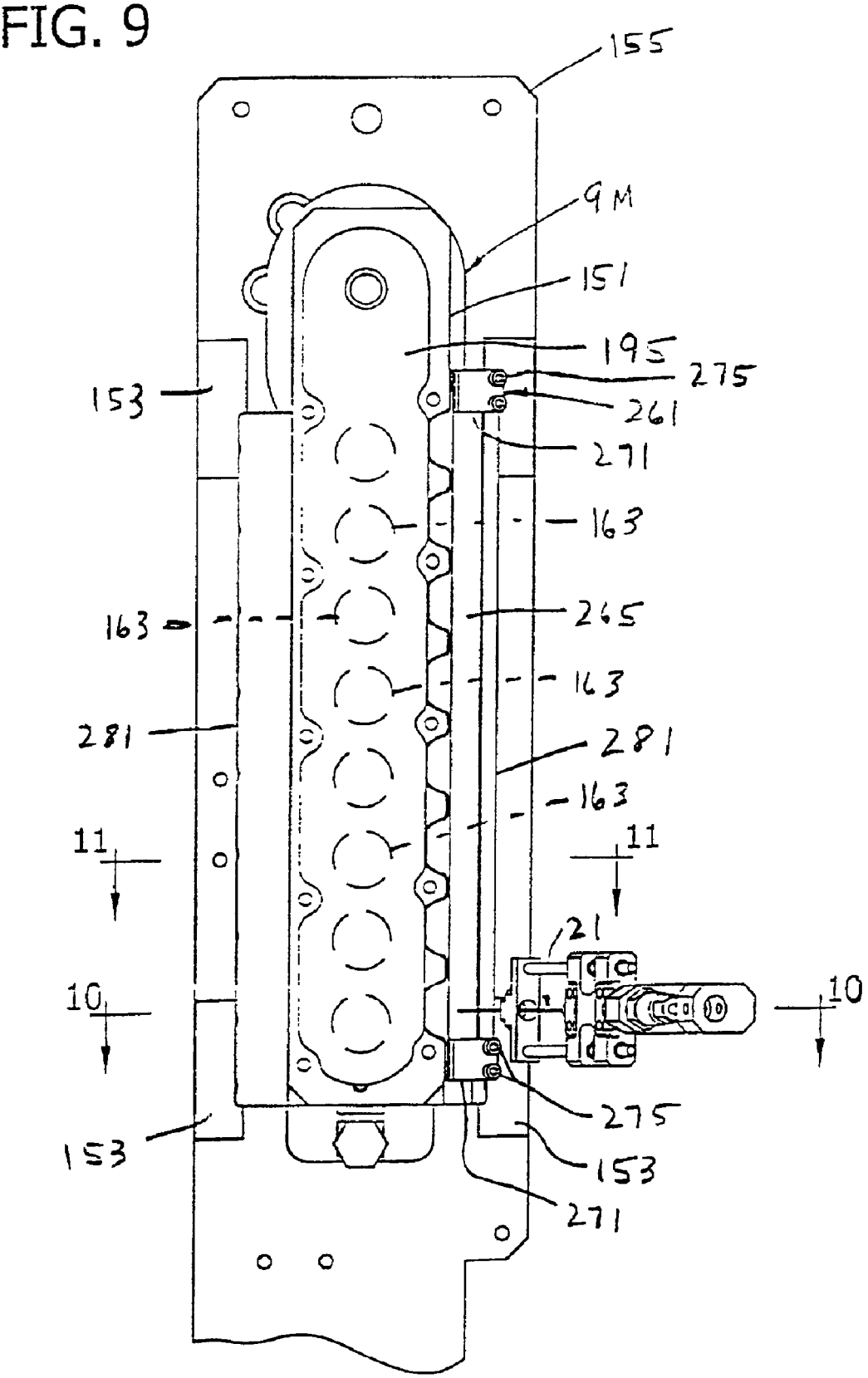
FIG. 9 is a top view of a reactor module showing a cannula immediately prior to the delivery of fluid to a vessel in the module.
Figure 10:
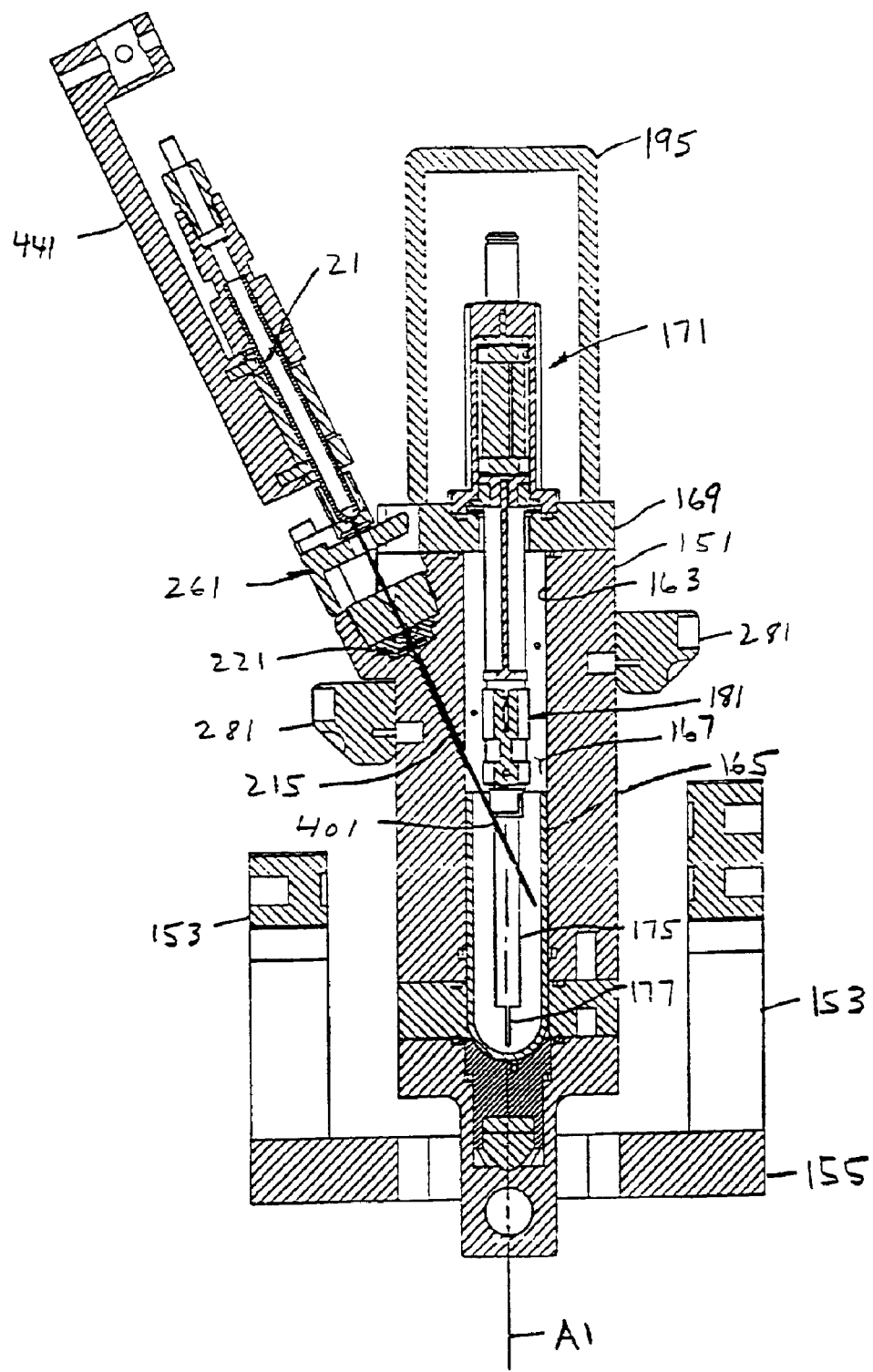
FIG. 10 is a vertical section along lines 10—10 of FIG. 9 showing the construction of a reactor module and cannula for delivering fluid (e.g., in slurry form) to a vessel in the reactor module.
Figure 11:
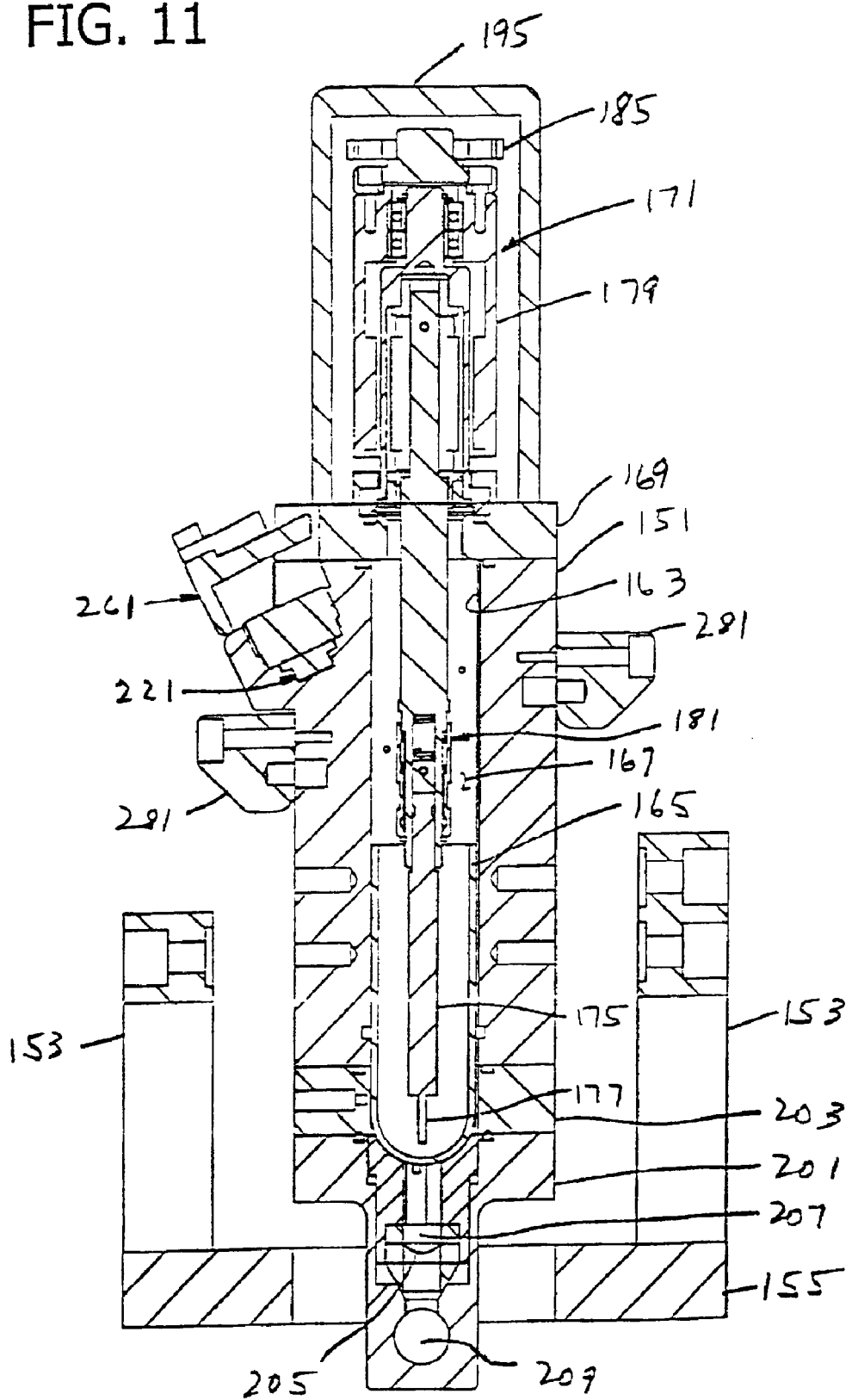
FIG. 11 is a vertical section on line 11—11 of FIG. 9 in a plane through the central axis of the vessel.

Referring now to FIGS. 9–11, each reactor module 9M comprises a reactor block 151 of suitable metal mounted on a pair of legs 153 secured to a base 155 which is fastened to a respective carriage plate 67b. The reactor block 151 is preferably mounted in a position spaced above the base so that it is thermally isolated from the base. Each reactor block 151 has two or more (e.g., eight) vessels therein formed by wells 163 each of which extends down from an upper surface of the reactor block and each of which has a central longitudinal axis A1 which is typically (but not necessarily) generally vertical. In the preferred embodiment, each well has a removable liner in the form of a reaction vial 165 for holding a reaction mixture to be processed. The reaction vial 165 may be of glass or other suitably chemically inert material capable of withstanding high-temperature chemical reactions. As used herein, the term "vessel" broadly means any structure for confining reaction materials in the reactor, including the walls defining the well 163, and/or the vial 165 or other liner in the well containing the reaction materials. In the embodiment shown in FIG. 10, the reaction vial 165 has a height substantially less than the height of the well 163, forming a head space 167 within the well above the vial, the head space and interior of the vial combining to form what may be referred to as a reaction chamber. This chamber is sealed closed by a header plate 169 releasably secured by suitable fasteners to the reactor block 151.

A stirrer mechanism, generally designated 171 in FIGS. 10 and 11, is provided for stirring the contents of each vessel. This mechanism preferably comprises a stirrer in the form of a shaft 175 having a mixing blade or paddle 177 thereon engageable with the contents of the vessel, and a magnetic drive 179 of the type described in the aforementioned International Application No. PCT/US 99/18358 (International Publication No. WO 00/09255) for rotating the stirrer at speeds in the range of 0 to about 3000 rpm, and preferably at a speed in the range of about 200–2000, and most preferably at a speed in the range of about 1000–2000.

Figure 5:
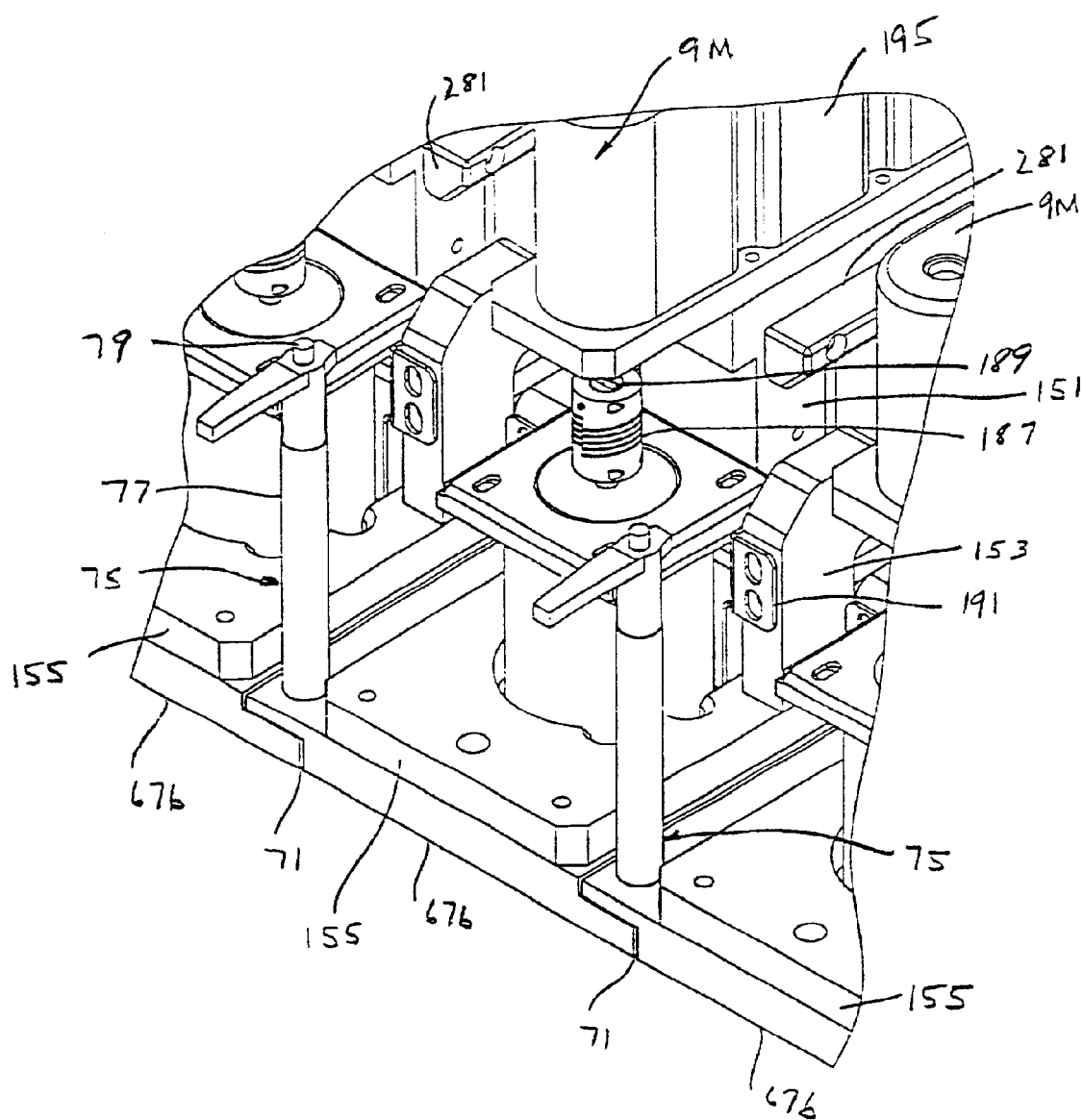
FIG. 5 is an enlarged portion of FIG. 3 showing several reactor modules mounted on a series of interconnected carriage plates.

The drive mechanism 179 is releasably coupled to the shaft 175 by a quick-acting coupling, generally designated 181, which may be of the type disclosed in the aforementioned International Application No. PCT/US 99/18358 (International Publication No. WO 00/09255) or in the aforementioned co-owned, pending application Ser. No. 60/255,716, filed Dec. 14, 2000. The magnetic drives 179 of the various stirrer mechanisms 171 of the reactor modules 9M are powered by a drive system comprising a gear train 185 (FIG. 11) releasably coupled to a stepper motor 187 by means of a key and shaft slip connection 189, as best illustrated in FIG. 5. The motor 187, in turn, is supported by brackets 191 fastened to the legs 153 extending up from the base on opposite sides of the reactor block 151. The gear train 185 and drive mechanisms 179 are enclosed by a cover 195 releasably secured to the header plate 169 on the reactor block 151. The arrangement is such that the stepper motor 187 rotates the gears of the gear train 185 to drive the magnetic drives 179 to rotate the stir shafts 175 in the vessels of the reactor module.

It will be understood that the stirrer mechanisms 171 may be rotated by other types of drive mechanisms. Also, each stirrer mechanism can be rotated by an independent drive system so that the rotational speed of the stirrer can be varied independent of the speed of the other stirrer mechanisms.

Referring to FIG. 11, a burst manifold 201 is secured to a spacer plate 203 attached to the bottom of the reactor block 151. The manifold 201 houses a series of disks 205, each of which is mounted in a passage 207 communicating with a respective well 163. In the event the pressure in a reaction chamber exceeds a predetermined pressure, the disk 205 is designed to rupture, which allows the chamber to vent into a vent passage 209 in the manifold communicating with a suitable vent system. The rupture pressure should be somewhat above maximum expected reaction pressures. In preferred embodiments, the reaction pressures are greater than atmospheric, preferably at least about 15 psig, more preferably at least about 50–100 psig, and yet more preferably up to about 500 psig or more.

In accordance with one aspect of the present invention, each reactor module 9M has a plurality of cannula passages 215 therein extending between an exterior surface of the reactor block 151 and the wells 163 formed in the reactor block, preferably one cannula passage 215 for each well. In the preferred embodiment shown in FIGS. 10 and 12, each cannula passage is straight and extends at an angle from a location adjacent the upper end of the reactor block 151 at one side thereof to a respective well 163 in the block, intersecting the side wall of the well in the head space 167 above the upper end of the mixing vial 165 in the well or, in the event a vial is not used, above the level of any liquid and/or solid reaction components in the well. The central longitudinal axis A2 of the passage 215 is at an appropriate angle θ relative to the central longitudinal axis A1 of the vessel, e.g., at a 25 degree angle off vertical, assuming the axis of the vessel is vertical (although it is not necessarily so). While the passage 215 shown in the drawings is straight, it will be understood that the passage need not be absolutely straight. For example, if the portion of the cannula 21 to be inserted into the passage is flexible or somewhat non-linear, the cannula passage 215 could also assume non-linear configurations (e.g., an arcuate configuration). However, in the preferred embodiment, the cannula passage is at least substantially straight, meaning that it is sufficiently straight to accommodate a cannula needle of the type to be described later in this specification.

The passage 215 is positioned so that when a respective cannula 21 is inserted into and through the passage 215, the distal end of the cannula is positioned inside the vessel, preferably inside the reaction vial 165 if one is used, for delivery of reaction material from the cannula at an elevation above any liquids and/or solids in the vial, and in a generally downward direction so that the reaction material exiting the cannula is delivered (transferred) into the vial without contacting any surface of the vial, as will be discussed later. The size and cross-sectional shape of the cannula passage 215 is not critical. By way of example, however, which is not intended to be limiting in any respect, the passage can be formed by a circular bore having a diameter which exceeds the outside diameter of cannula 21 by about 0.032 in. The angle θ of the cannula passage 215 may also vary, depending on the spacing between adjacent reactor modules 9M, the height of the reactor module, the size of the vessels, and other factors. In the preferred embodiment, all cannula passages 215 extend from an exterior surface of the reactor block 151 on the same side of the block, but it will be understood that the cannula passages for different wells 163 could extend from different sides of the reactor block without departing from the scope of this invention.

Figure 12:
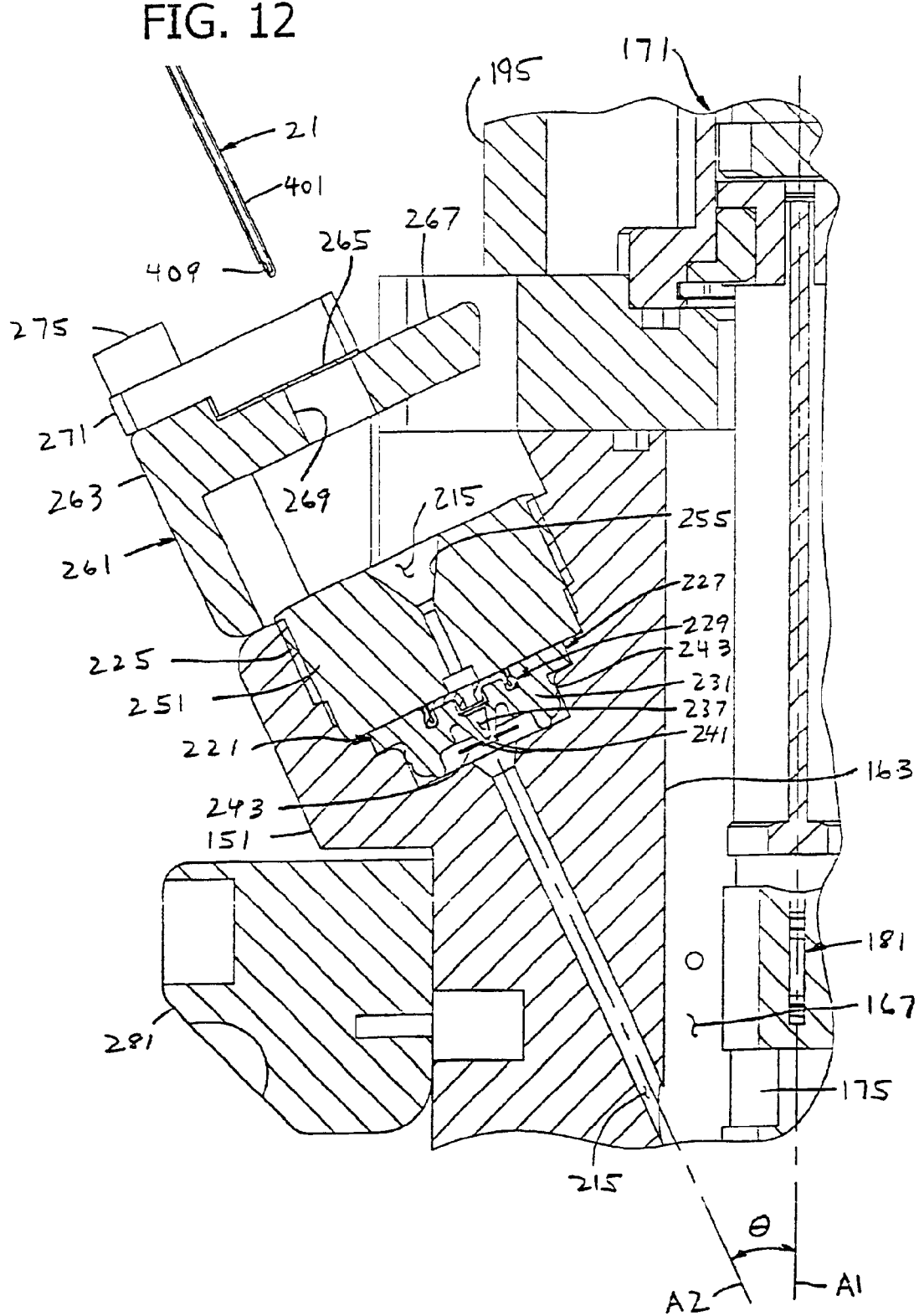
FIGS. 12–14 are sequential views illustrating various steps in the procedure for delivering fluid to a vessel via the cannula.
Figure 13:
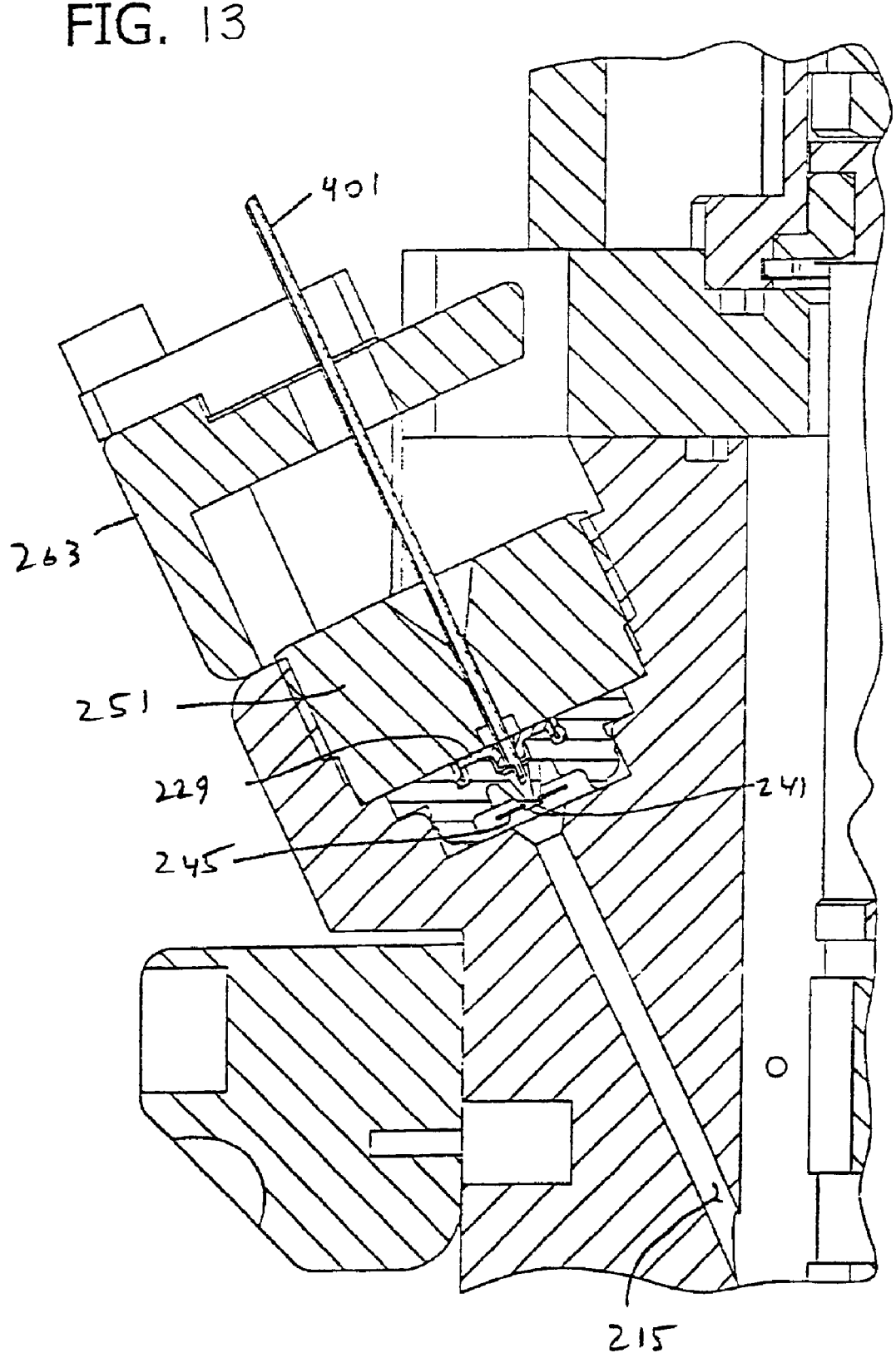
Figure 14:
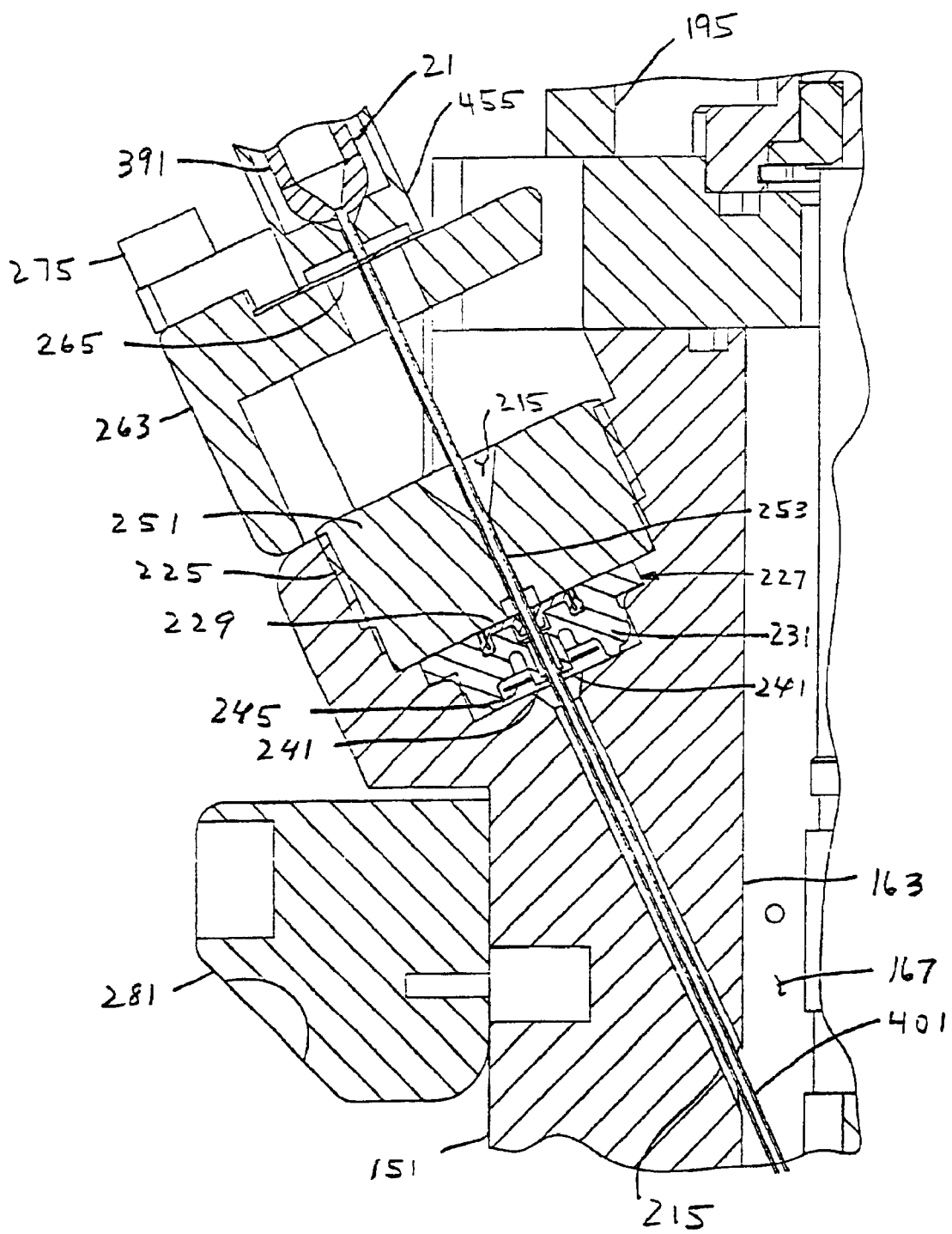

A sealing mechanism, generally designated 221 in FIG. 12, is provided in each cannula passage 215 for maintaining the reaction vessel sealed against ambient conditions when the cannula is inserted into and withdrawn from the cannula passage, thus preventing any substantial pressure losses if the pressure in the reaction vessel is positive, or any pressure gains if the pressure in the reaction vessel is negative with respect to ambient pressure. As shown best in FIGS. 12–14, the sealing mechanism 221 is located in the passage 215 adjacent its upper end at the entry port thereof which is enlarged by a counterbore 225 to accept the mechanism. The mechanism 221 includes a valve 227 movable between a closed position for closing the cannula passage 215 and an open position permitting movement of the cannula through the passage, and a seal 229 in the passage sealingly engageable with the cannula 21 when the valve 227 is in its open position. The valve 227 and seal 229 may be separate elements or formed as a single unit. In the preferred embodiment, the valve and seal are fabricated as a single assembly of the type described in U.S. Pat. No. 4,954,149, incorporated herein by reference, owned by Merlin Instrument Company of Half Moon Bay, Calif. In this (FIG. 12) embodiment, the valve 227 has a body 231 molded from suitable material (e.g., Viton® fluorocarbon rubber) received in a counterbore 233 in the reactor body 151, a sealing ridge 235 extending circumferentially around the body 231 for sealing against the reactor body, a central passage 237 through the body forming part of the cannula passage 215, a duckbill valve comprising a pair of duckbill lips 241 formed integrally with the valve body 231, and a metal spring 243 (e.g., of hardened stainless steel) which biases the lips 241 together to close the passage 237. The lips 241 are forced open against the bias of the spring by the distal end of the cannula 21 as it is inserted through the passage 237 in the valve body (FIG. 13). The lips 241 have a sliding fit against the cannula as it is so inserted. The first-mentioned seal 229 is an annular seal on the body immediately above the valve formed by the duckbill lips 241 on the side of the valve opposite the vial 165 in the well. The annular seal 229 is sized for sliding sealing engagement with the cannula 21 as the cannula is withdrawn from the reactor, since it may take some very small period of time for the lips 241 of the duckbill valve to close after the cannula is pulled past the lips. The sealing mechanism 221 is held in place by a nut 251 threaded in the counterbore 225 in the reactor block 151 into engagement with a circular sealing ridge (not shown) on the upper face of the valve body 231. As shown in FIG. 12, the nut 251 has a central bore 253 therethrough aligned with the passage 237 through the valve body 231. The upper end of this bore which constitutes the entry port of the cannula passage 25, is tapered to provide a lead-in 255 for the cannula.

A wiper assembly, generally indicated at 261, is provided adjacent the upper (inlet) end of each cannula passage 215 (see FIGS. 9 and 12). The assembly 261 comprises a wiper frame 263 mounted on the reactor module 9M immediately above the inlets of the cannula passages 215, a wiper member 265 overlying a leg 267 of the frame having one or more openings 269 therein in registry with the upper entry end of the cannula passages 215, a clamp member 271 overlying the wiper member 265, and fasteners 275 (only one shown in FIG. 12) for tightening the clamp member 271 on the frame 263 to clamp the wiper member 265 in place. The wiper member is of a material capable of being penetrated by the distal end of the needle of the cannula 21 and then wiping reaction material off the exterior surface of the needle as it is moved down into the cannula passage 215. The removal of reactant material before entry of the cannula into the cannula passages is important, especially when handling slurries containing small solid particles, since such particles could interfere with the sealing mechanisms 221 in the passages 215. One material found to be suitable as a wiper member is an expanded Teflon® gasket material sold by W.L. Gore & Associates, Inc. Other materials (e.g., silicone rubber) may also be used. Preferably, the wiper member 265 comprises a single strip of material which extends the length of the reactor block 151 at one side of the block and overlies the openings 269 at the upper ends of all cannula passages 215 in the block (see FIGS. 9 and 12). Alternatively, the wiper member 265 can comprise separate pieces for the separate cannula passages 215. The wiper frame 263 is removably mounted on the reactor block 215 so the wiper member 265 can be easily replaced after each run. In the preferred embodiment, the frame 263 sits on pins (not shown) on the reactor block 151 and is easily removed simply by lifting the frame off the pins.

Gas manifolds 281 extend along opposite sides of the reactor block 151, as shown in FIGS. 9 and 10. Process gas lines 57 extending from fittings 55 on the enclosure 31 communicate with one manifold (the right manifold as shown in FIG. 10) to provide for the delivery of process gas (e.g., reactant gas such as ethylene or propylene) to the vessels in the reactor module 9M. Lines 57 extending from the fittings 55 on the enclosure to the other (left) manifold 281 provide for the delivery of quenching or inert gas (e.g., carbon dioxide) to the vessels to terminate a reaction and/or to vent the gaseous contents of the vessel. Flow through the lines 57 to the manifolds 281 is controlled by solenoid valves 285 mounted on the bore 155 immediately adjacent the reactor module (FIG. 4).

Figure 15:
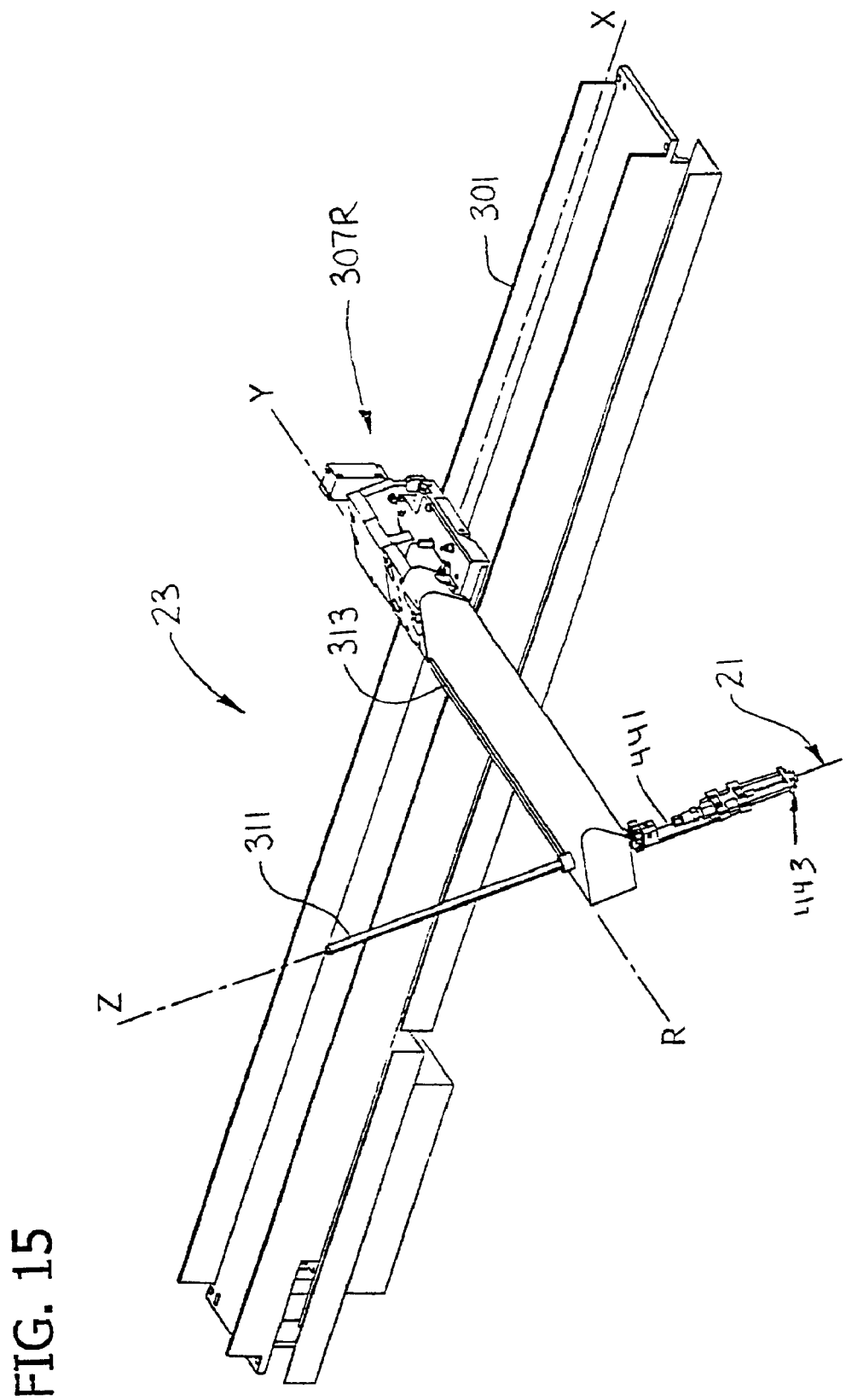
FIG. 15 is a perspective of key components of the robot system, showing the cannula in a travel position with the head of the support in a lowered position down on the needle of the cannula.
Figure 16:
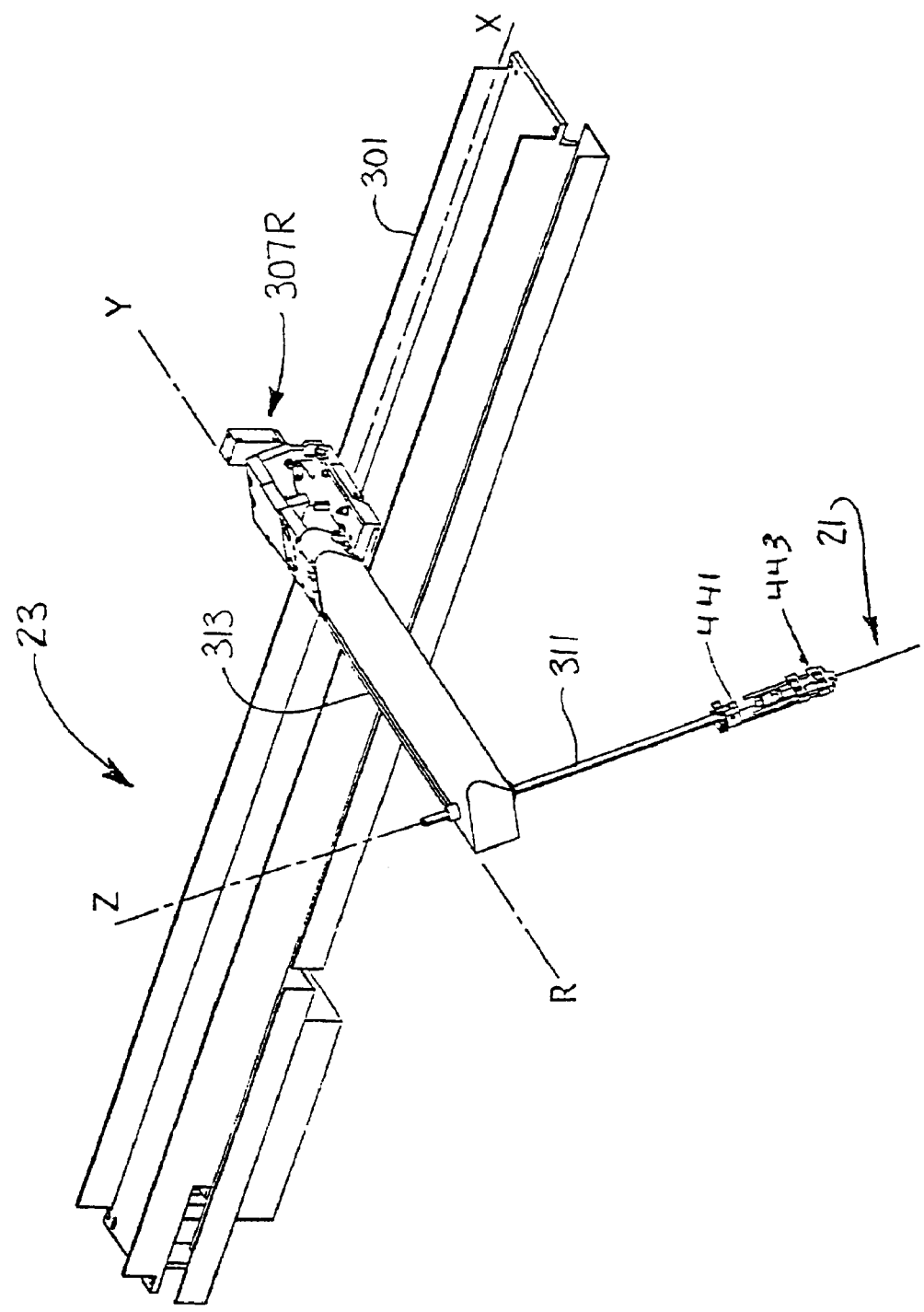
FIG. 16 is a view similar to FIG. 15 showing the cannula in a fluid delivery position, with the head of the support in a raised position up on the needle.

In general, the robot system 23 is a conventional three-axis system providing translational movement along X, Y and Z axes (see FIGS. 15 and 16), except that the system is modified as described hereinafter to provide for rotational movement about a fourth axis R, which may intersect axis Z. The conventional three-axis system referred to may be a system commercially available from Cavro Scientific Instruments of Sunnyvale, Calif., Model No. 727633. Referring to FIG. 3, the robot system 23 in one embodiment comprises a horizontal track 301 mounted on the enclosure 3 by brackets 303, left and right carriages 305b, 305a mounted on the track for linear movement along the X axis, and left and right robot arms 307L, 307R extending from respective carriages. (As referred to herein, left and right is as viewed in FIGS. 1, 3, 15 and 16.) An elongate rack 311 on each arm 307L, 307R carries a respective cannula 21. The rack 311 is mounted for movement in a slot 313 in the robot arm along the Y axis, and is also engageable with a drive pinion (not shown) in the arm for movement along the Z axis. In accordance with another aspect of this invention, the carriage 305L, 305R associated with each robot arm 307L, 307R is modified to provide for rotation of the arm about axis R. Since the left and right carriages may be of somewhat different construction, both will be described.

Figure 17:
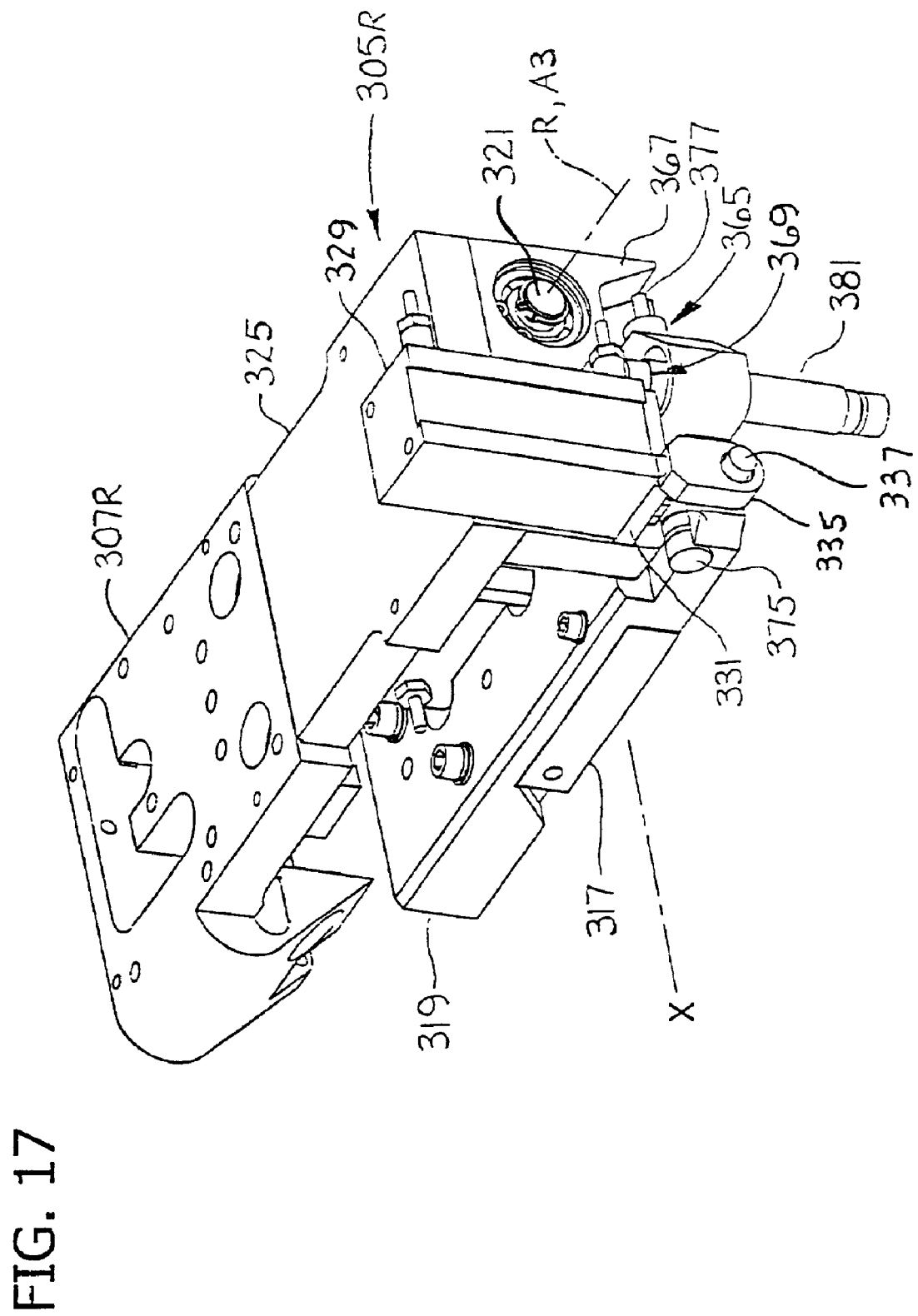
FIG. 17 is a perspective showing a mechanism for rotating the right robot arm about its axis, the mechanism being shown in a flat or non-rotated position.
Figure 18:
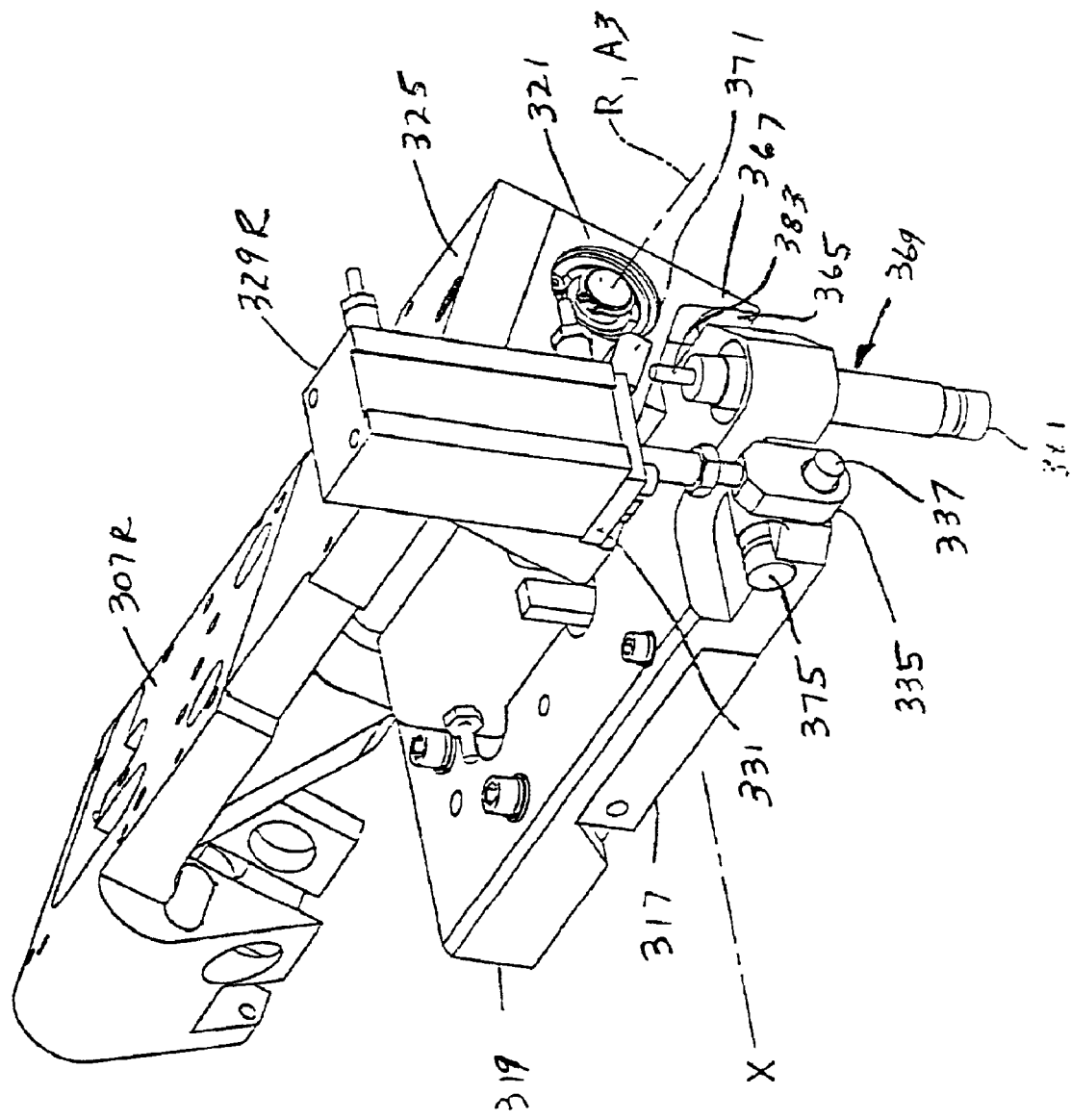
FIG. 18 is a view similar to FIG. 17 showing the mechanism in a rotated position.
Figure 19:
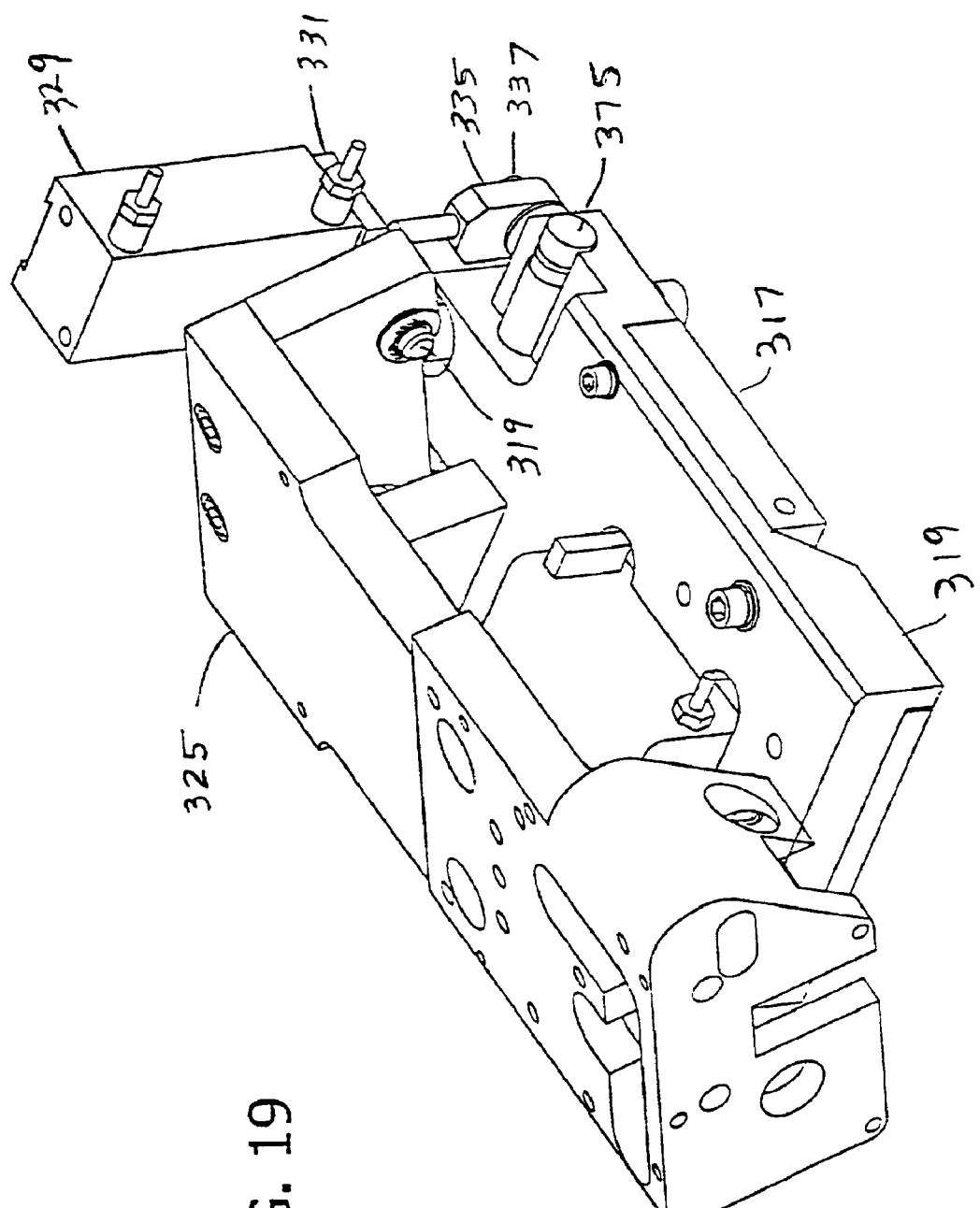
FIG. 19 is a view similar to FIG. 18 but showing the mechanism as viewed from an opposite end of the mechanism.

The construction of the right carriage 305R is shown in FIGS. 17–19. The carriage comprises a slider 317 engageable in conventional fashion with the track 301, a base 319 affixed to the slider, a shaft 321 mounted on the base having a longitudinal axis A3 corresponding to axis R, and a pivot block 325 mounted on the shaft for rotation on axis R. The pivot block 325 carries the right robot arm 307R and is rotatable by a power actuator which, in the preferred embodiment, is a double-acting pneumatic cylinder 329R. The cylinder 329R is mounted on a platform 331 pivotally secured at 333 in FIG. 19 to the pivot block 325 and has a rod end having a clevis pivot connection 335 with a shaft 337 extending from the base 319, the arrangement being such that the extension of the cylinder rod causes the pivot block 325 to rotate in a first (clockwise) direction from the generally horizontal "home" position shown in FIG. 17 to the tilted position shown in FIG. 18, and retraction of the rod causes the pivot block to rotate in the opposite (counterclockwise) direction. During such extension and retraction, the platform 331 pivots relative to the pivot block 325 and the clevis connection 335 rotates on the shaft 337. Extension and retraction of the cylinder 329R is controlled by a suitable pneumatic system, one such system being designated 341 in FIG. 2. In this embodiment, an inert gas (e.g., argon or nitrogen) is supplied to opposite ends of the cylinder 329R by two lines 343, 345, the first of which (343) supplies gas at a relatively high pressure (e.g., 60 psig) to one end of the cylinder for extending the cylinder to rotate the pivot block 325 to its angled (tilted) position, and the second of which (345) supplies gas at a lower pressure (e.g., 40 psig) to the opposite end of the cylinder. Both gas lines 343, 345 are connected to a suitable source 351 of high pressure gas (e.g., argon or other inert gas). Regulators 353 are used to control the pressure in the lines 343, 345. A solenoid valve 357 in line 343 controls the supply of high pressure gas to the cylinder 329R. Both lines contain orifices 361 adjacent the cylinder 329R to restrict the flow of gas to dampen the movement of the cylinder, and thus the rotational movement of the pivot block 325 and robot arm 307R. When the solenoid valve 357 is open to provide high pressure gas to the cylinder, the piston of the cylinder extends against the lower pressure gas to rotate the pivot block 325. When the solenoid valve 357 is closed, gas is vented from the high-pressure end of the cylinder 329R, allowing the piston to move in the opposite direction under the influence of the lower pressure gas to rotate the pivot block 325 in the opposite direction. Other pneumatic circuits may be used. Similarly, other types of power actuators may be used for rotating the pivot block 325. Further, other damping means may be used to dampen the rate of pivotal movement of the pivot block 325 and robot arm 307R about axis R. For example, a suitable damping device could be positioned between the pivot block 325 and the base 319.

The range of rotational movement of the pivot block 325 is determined by stops (see FIGS. 17 and 18). In the preferred embodiment, movement in the clockwise direction is determined by the location of a first adjustable stop 365 on the base 319 engageable by a first stop 367 on the pivot block 325, and rotational movement of the pivot block in the counterclockwise direction is determined by the location of a second adjustable stop 369 on the base engageable with a second stop 371 on the pivot block.

The first adjustable stop 365 comprises a damping cylinder 375 mounted on the base 319 in a generally horizontal position, and a rod 377 (FIG. 17) extending from the cylinder having an upper end engageable by the first stop 367 on the pivot block 325. The cylinder 375 has a threaded connection with the base 319 so that the cylinder may be moved along its axis to adjust the axial position of the rod 377. A jamb nut (not shown) may be used to secure the cylinder in adjusted position. The damping cylinder 375 contains fluid movable through an optimally adjustable orifice to damp movement of the rod 377 as it moves to its final fixed position, as will be understood by those skilled in the art. The cylinder and rod are of conventional design. A suitable damping cylinder 375 is commercially available from Humphrey of Kalamazoo, Mich., Part No. HKSH5X8.

The second adjustable stop 369 is similar to the first adjustable stop 365 described above except that the cylinder (designated 381) is mounted in a generally vertical position for engagement of its rod 383 by the second stop 371 on the pivot block 325.

It will be understood, therefore, that the range of rotational movement of the pivot block 325 can be adjusted by setting the location of the adjustable stops 365, 369 to the desired locations. In the preferred embodiment, the range of motion is through a range of about 25 degrees, preferably between a position in which the cannula 21 is vertical and one where the cannula is 25 degrees off vertical, although this range may vary without departing from the scope of this invention. Whatever the range, the pivot block 325 in its tilted position should rotate the robot arm 307R to a position in which the cannula 21 is held at an angle corresponding to the angle of the cannula passages 215 in the reactors 9M so that the cannulas can be inserted through the passages.

The range of rotational movement of the pivot block 325 can be limited in other ways without departing from the scope of this invention.

Figure 20:
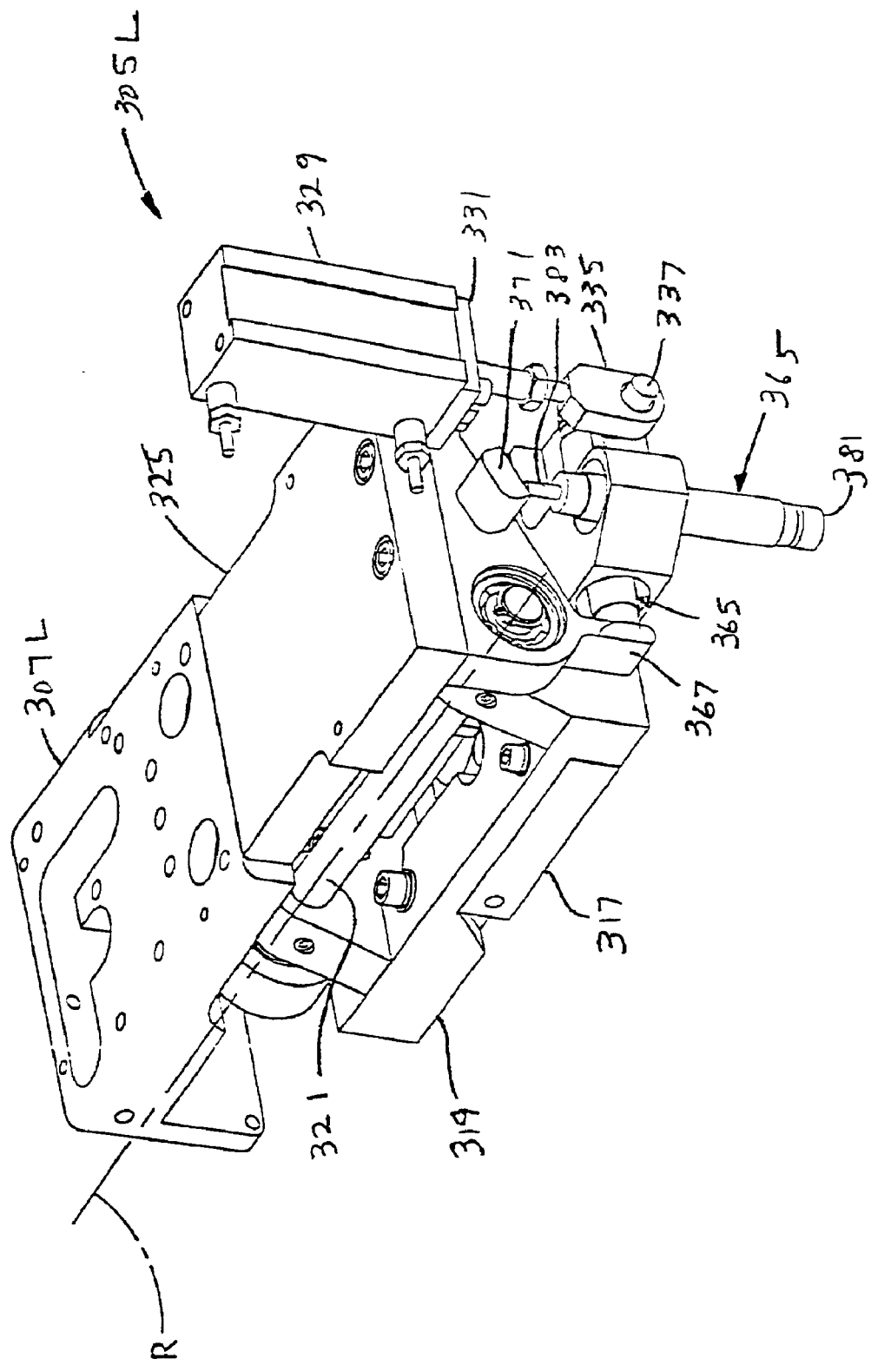
FIG. 20 is a perspective showing a mechanism for rotating the left robot arm about its axis, the mechanism being shown in a flat or non-rotated position.
Figure 21:
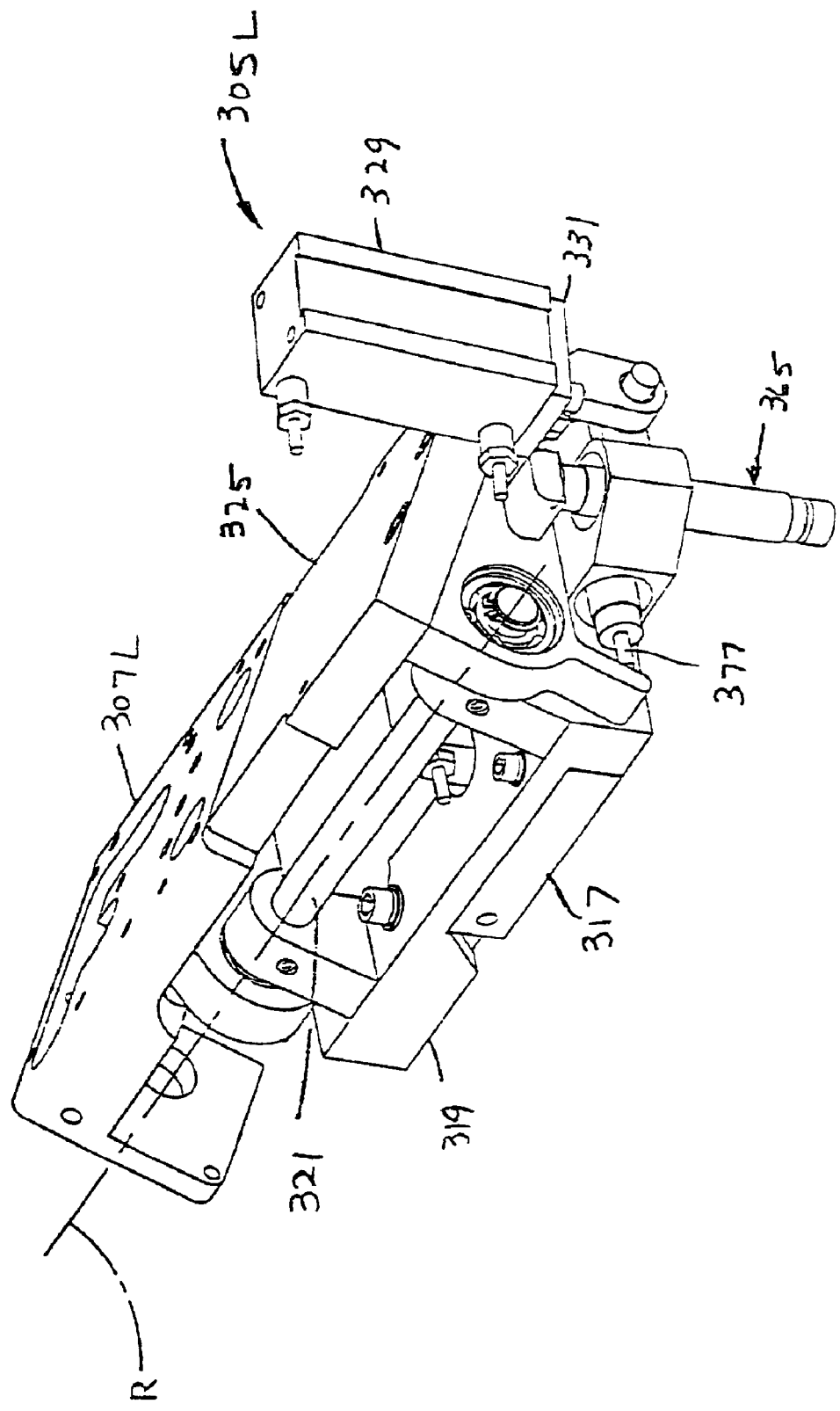
FIG. 21 is a view similar to FIG. 20 showing the mechanism in a rotated position.
Figure 22:
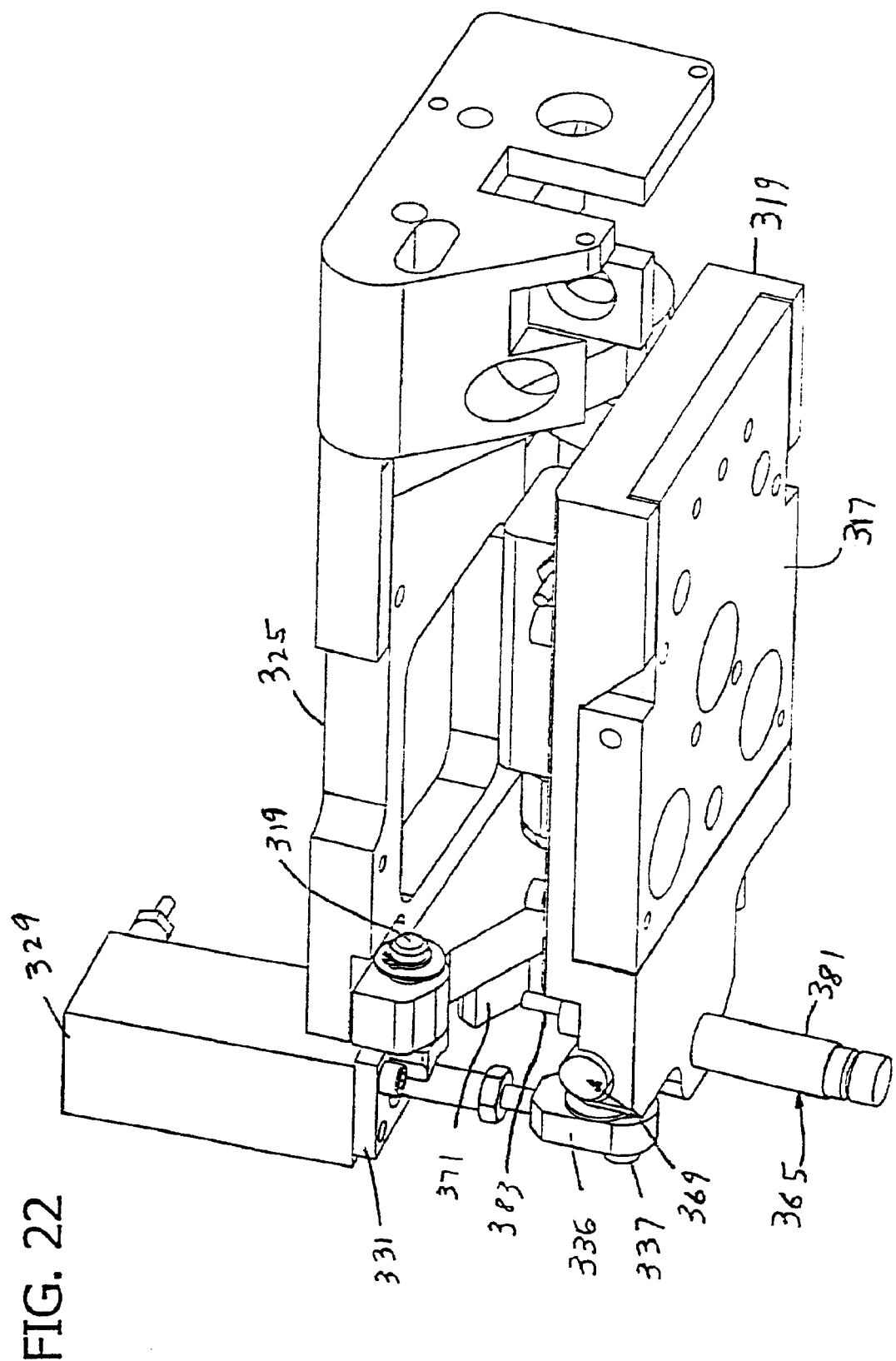
FIG. 22 is a view similar to FIG. 20 but showing the mechanism as viewed from below.

The left carriage 305L for the left robot arm 307L is shown in FIGS. 20–22. The construction of the left carriage is very similar to the construction of the right carriage 307R, and corresponding parts are designated by the same reference numbers. However, there are some differences between the two carriages even though the left and right robot arms are mirror images of one another. This is because, in the preferred embodiment shown in the drawings (e.g., FIG. 9), the entry ports of the cannula passages 215 of the reactor modules 9M all face in the same lateral direction, i.e., toward the left end of the dry box 3 shown in FIG. 1. Another reason for the different construction is the preference to maintain the R-axis of rotation of each robot arm 307L, 307R in line with the Z-axis of travel to reduce the complexity of the motion control for the robot. In any event, the most significant difference in construction is that, for the left carriage 305L, the pivot shaft 321 is on the opposite side of the base 319, and the cylinder 329 is mounted so that retraction of the cylinder causes the pivot block 325 (and the left robot arm 307L) to rotate from its home position shown in FIG. 20 to its angled position shown in FIG. 21, and extension of the cylinder causes the pivot block to rotate from its angled position back to its home position.

It will be understood that the construction of the left and right carriages 305L, 305R could be different from that shown without departing from the scope of this invention.

Figure 23:
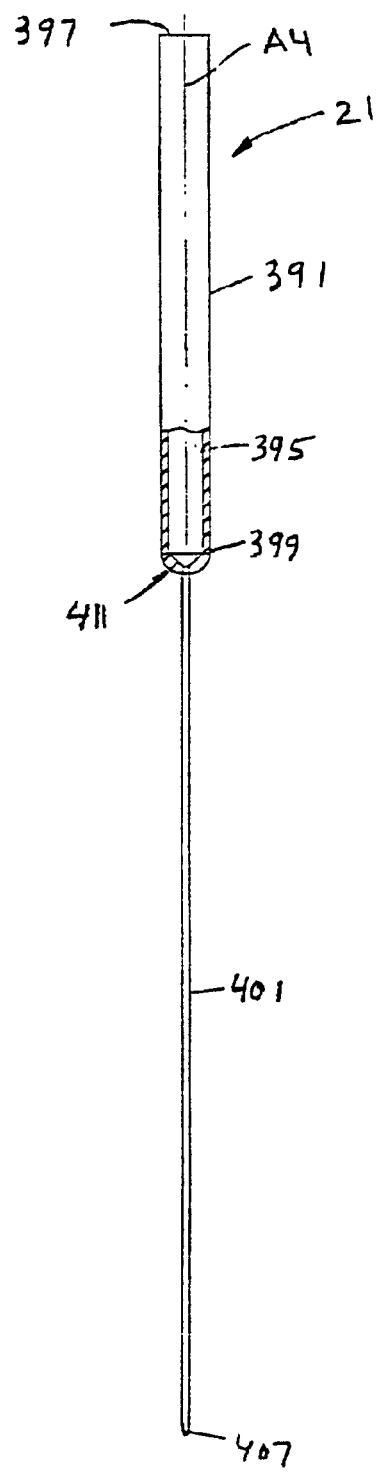
FIG. 23 is a side elevation of the cannula, with part of the cannula being shown in section to illustrate details.
Figure 23A:
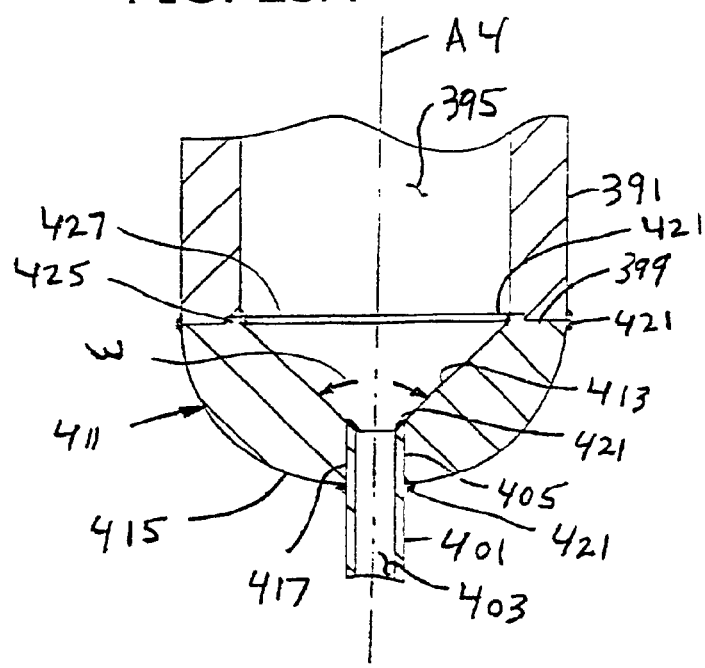
FIG. 23A is an enlarged view showing details of the construction of the cannula of FIG. 23.
Figure 24:
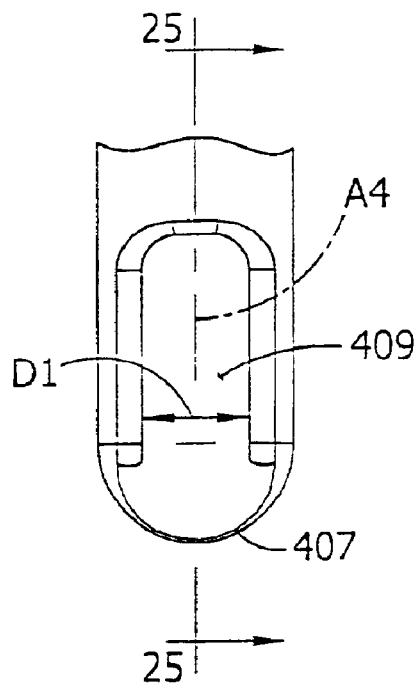
FIG. 24 is an enlarged view of a port of the cannula.
Figure 25:
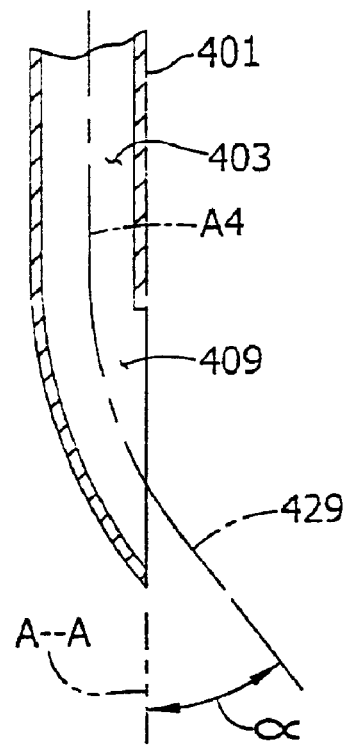
FIG. 25 is a section taken on line 25—25 of FIG. 24.

A cannula 21 used in the apparatus of the present invention is shown in FIGS. 23–25. The cannula includes a hollow tubular reservoir 391 having a central longitudinal axis A4, an outside dimension (e.g., circular diameter), an inside dimension (e.g., circular diameter) defining a hollow interior 375, a proximal (upper) end 397 and a distal (lower) end 399. The cannula also includes a long thin straight tube 401 (hereinafter referred to as a "needle") extending coaxially with respect to the reservoir 391. The needle 401 has an outside dimension (e.g., circular diameter) substantially less than the outside dimension of the reservoir 391, an inside surface (e.g., circular diameter) which defines a central flow passage 403 extending the length of the needle, an open proximal (upper) end 405 which communicates with the hollow interior 395 of the reservoir, a lower distal end 407, and a port 409 adjacent the distal end which opens laterally (i.e., to the side) relative to the aforementioned axis. The upper end 405 of the needle 401 is joined to the lower end 399 of the reservoir 391 by means of a bowl-shaped metal transition, generally designated 411, having a sloping, funnel-shaped interior side wall 413 and a bottom 415 having a hole 417 therein for snugly receiving the upper end portion of the needle, the upper end 405 of the needle being flush with the interior surface of the transition. The transition is joined to the reservoir and the needle by welds indicated at 421 in FIG. 23A. These weld areas, and the entire interior surface of the transition and adjacent surfaces of the reservoir and needle, are polished to a high degree of smoothness so that the interior surfaces of the reservoir, transition and needle form a continuous expanse of smooth surface area without crevices or other surface discontinuities which might trap particles or other material which could interfere with aspiration into the needle or delivery from the needle in accurate quantities. The exterior surfaces of the reservoir 391, transition 411 and needle 401 should be similarly polished.

By way of example, the reservoir 391 is formed from metal, preferably stainless steel tubing having, for example, an outside diameter in the range of about 0.05 to 0.50 in, more preferably in the range of about 0.05–0.25 in, and most preferably about 0.188 in.; an inside diameter in the range of about 0.02–0.45 in, and more preferably about 0.118 in.; and a length in the range of about 1.0–6.0 in, more preferably about 2.0 in. The volume of the reservoir 391 should be substantially greater than the largest volume of material to be aspirated into the cannula 21 (e.g., preferably in the range of about 10 μl–5000 μl, more preferably in the range of about 25 μl–3500 μl, and most preferably about 350 μl).

The needle 401 is preferably also formed from metal tubing having, for example, an outside diameter in the range of about 0.01–0.15 in., more preferably about 0.02–0.10 in, and still more preferably about 0.028 in.; an inside diameter in the range of about 0.005–0.12 in., more preferably about 0.01–0.09 in., and still more preferably about 0.0155 in.; and a length in the range of about 1.5–5.0 in, more preferably in the range of about 2.0–4.0, and most preferably about 3.4 in. The port 409 of the needle, shown best in FIG. 24, is generally oval in the shape of a racetrack and is sized to have a minimum dimension D1 substantially larger (e.g., four times larger) than the largest particle of material to be handled by the cannula. For example, a port 409 having a minimum dimension of about 0.0155 has been found to be acceptable for handling slurries containing silica particles averaging 10–100 microns in diameter. Other shapes and dimensions may be suitable, depending on the type of material being handled. The transition 411 is preferably of the same metal as the needle 401 and reservoir 391, e.g., stainless steel, and has a suitable axial length (e.g., preferably in the range of 0.10–0.50 in., and more preferably about 0.215 in.) The exact shape of the transition is not believed to be critical, so long as the inside surface of the transition is contoured for funneling material from the reservoir to the needle to provide for efficient flow between the reservoir and needle (e.g., no air pockets or other dead volume or space). The interior surface of the transition 411 should also be smooth to minimize any discontinuities or other surface variations which would otherwise tend to trap material. In the preferred embodiment, the interior wall 413 of the transition 411 is generally conical with an included angle $\omega$ in the range of about 20–70 degrees, and more preferably about 30 degrees, although other angles of inclination may also be used. The upper end of the transition 411 is formed with an upwardly projecting annular shoulder 425 received in a shallow counterbore 427 in the lower end 399 of the reservoir 391 to ensure proper registration between the two members when they are secured together, as by laser welding. The OD of the transition 411 is preferably substantially the same as the OD of the reservoir 391, and the ID of the transition at its upper end is preferably the same as the ID of the reservoir at its lower end.

The cannula 21 can be fabricated as follows. The needle 401 is made by bending the end of a length of straight metal tubing and cutting the distal end of the tubing along a line A—A (FIG. 25), parallel to the axis A4 of the tubing, to form the laterally opening port 409. To insure that the port 409 opens substantially downwardly when the needle is inserted in the cannula passage 215, the angle α between the cut line A—A and the bend radius 429 should substantially correspond to the angle A of inclination of the passage 215. The proximal (upper) end 405 of the tube is then inserted into the hole 417 in the bottom of the transition 411 and welded in position along weld lines 421 on the inside and outside of the transition. The inside and outside surfaces of the transition and welded areas of the needle are subjected to a grinding/polishing procedure to provide a smooth finish in which the upper end of the needle is flush with the inside surface of the transition, and in which all surfaces and junctures are completely smooth. The distal end 407 of the needle 401 at the port 409 are also polished. The transition 411 is then welded to the tubular reservoir 391. A final polishing operation smooths the weld areas at the juncture between the transition 411 and the reservoir 391, and the inside and outside surfaces of the reservoir.

The cannula 21 can be fabricated in other ways. However, it is important that the cannula needle have a laterally opening port so that when the needle is inserted through the cannula passage 215 and into the reaction chamber, fluid reaction material (e.g., slurry material) is delivered from the port in a downward direction onto the interior bottom surface of vial 165 or the surface of the contents in the reaction vial rather than onto the side wall of the vial. Further, it is important that a reservoir be provided above the needle to insure that reaction materials aspirated into the needle are fully contained without backing up into the flow lines of the system.

A flow line 431 (e.g., flexible plastic tubing) is secured to the upper open end of the reservoir 391 by means of a fitting 433 having a sealing connection with the upper end of the reservoir and the flow line (FIGS. 26 and 27). This connection is effected by means of a compression nut 435 threadable on the fitting 433. The nut 435 is designed so that when it is turned, it squeezes against the flow line 431 and reservoir 391 to provide a sealing connection of the line to the reservoir for the flow of working fluid (e.g., solvent) between the pump 43 and the cannula 21, as occurs during operation of the system.

Again referring to FIGS. 26 and 27, each cannula 21 is mounted on a respective robot arm 307R, 307L by means of a mount comprising a bracket 441 secured at its upper end to the elongate rack 311 extending down from the robot arm, and a cannula support 443 secured to the bracket 441 for supporting and stabilizing the cannula as it is moved. More particularly, the cannula support 443 comprises a yoke-like body 445 which is mounted on locating pins 446 projecting forward from the bracket and secured in position to the bracket by suitable fasteners (e.g., socket-head cap screws, not shown). The body 445 has a vertical bore 447 through it for receiving the reservoir 391 of the cannula therein, a pair of recesses 449 in the front face of the body 445 exposing portions of the reservoir, a pair of clamping plates 451 received in the recesses and engageable with the exposed portions of the reservoir, and clamping screws (not shown) extending through clearance holes 453 in the clamping plates and threadable into the body 445. The clamping screws are tightened to draw the clamping plates toward the body to clamp the reservoir in fixed position against the body. The cannula should be secured in a position wherein the port 409 at the distal end 407 of the needle 401 faces in a generally downward direction when the cannula is in its fluid delivery position.

Figure 28:
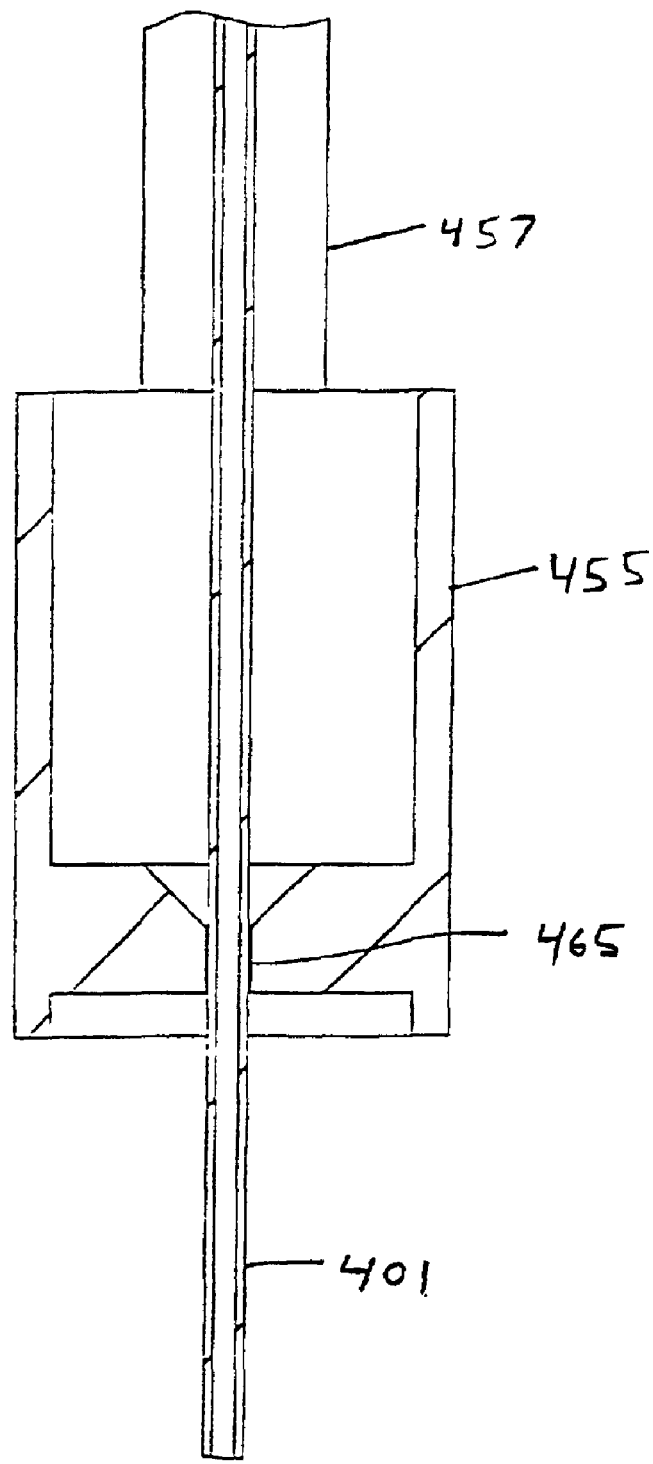
FIG. 28 is an enlarged portion of FIG. 27 showing a head of the support.

The cannula support 443 also includes a head 455 fixedly mounted on a pair of parallel guide rods 457 which are slidable in bushings (not shown) in bores of arms 463 extending laterally from opposite sides of the support body 445. The head 455 has a central bore 465 therein (FIG. 28) sized for a close clearance fit with the needle 401 of the cannula at a position intermediate the ends of the needle. The head 455 is movable relative to the body 445 from a lowered position (shown in solid lines in FIG. 26) in which the head is spaced from the body for engagement with a more distal portion of the needle 401, and a raised position (shown in phantom lines) in which the head is closer to the body for engagement with a more proximal portion of the needle to allow for insertion of the said more distal portion of the needle into a cannula passage 215. The head 455 and guide rods 457 affixed thereto are biased by gravity toward the lowered position. A retaining ring (not shown) on at least one of the guide rods 457 is engageable with the support body 445 for limiting the downward movement of the head. The close clearance fit of the needle 401 in the bore 465 of the head (FIG. 28) maintains the needle in the required precise angular position, and also stabilizes the needle to prevent buckling of the needle in use, as when the needle is pushed to penetrate the sealing mechanism 221. (This mechanism may be resistant to penetration if the pressures in the reactor chamber is large.) Preferably, the bore 465 in the head 455 is sized to be about 0.001–0.010 in. larger than the OD of the needle 401, and more preferably about 0.004 in. larger.

Figure 29:
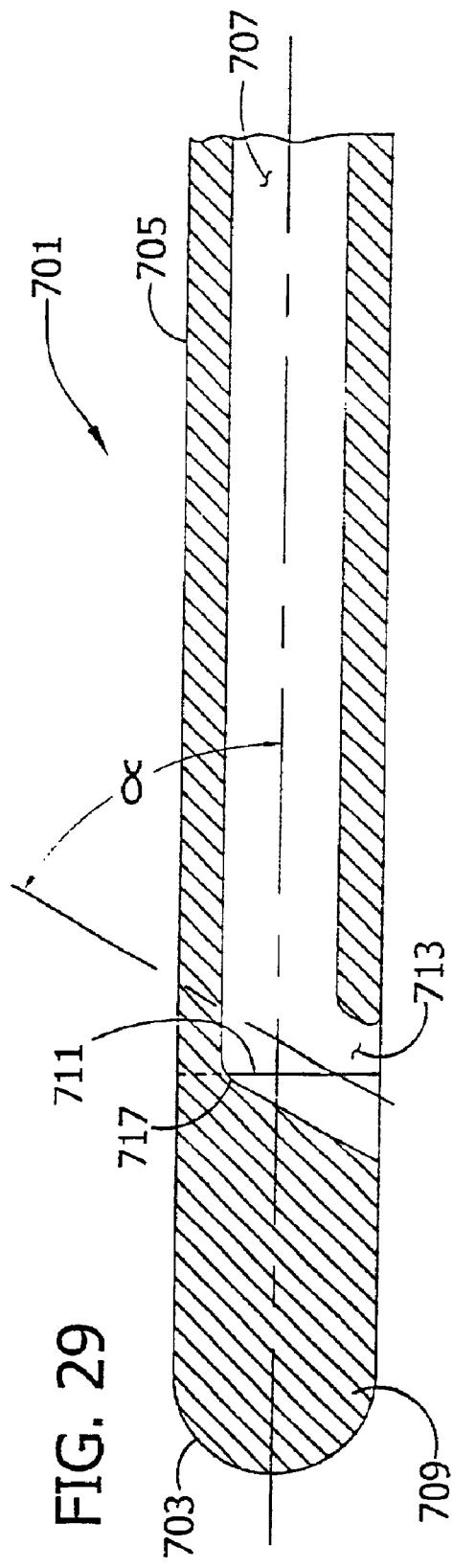
FIG. 29 is a partial sectional view of a cannula having an alternative needle configuration.
Figure 30:
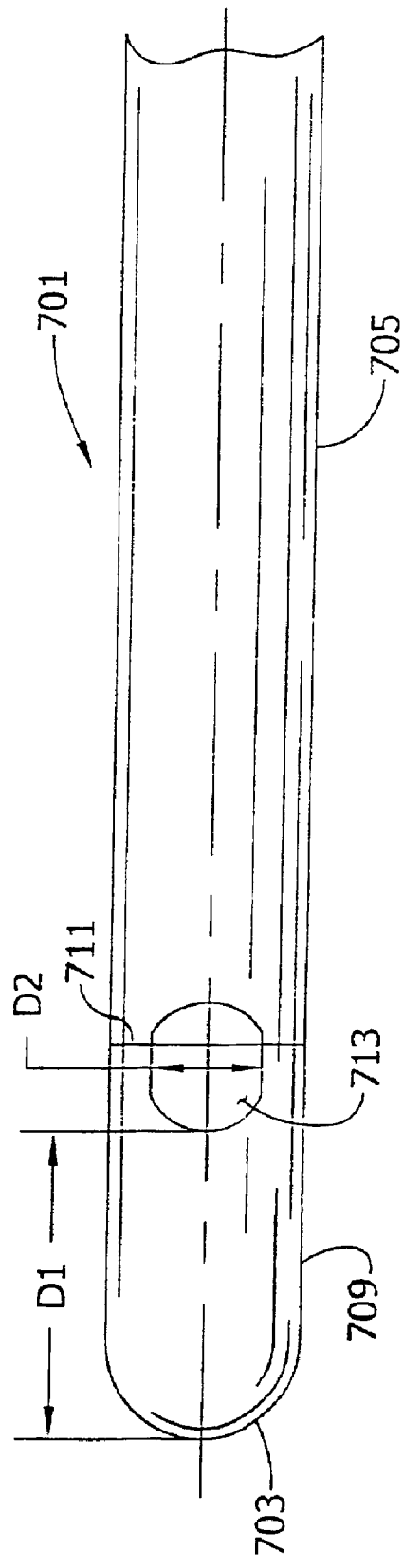
FIG. 30 is of a partial view of the needle and port of the cannula of FIG. 29.

FIGS. 29 and 30 illustrate an alternative cannula design in which the needle, generally indicated at 701, has a different end configuration. In this embodiment, the tip of the needle is rounded as indicated at 703, preferably having a generally hemispherical shape. The bluntness of this configuration reduces the wear on the sealing mechanism 221 (compared to prior designs) during insertion of the needle into the cannula passages 215. While the specific construction of the needle 701 may vary, in the embodiment of FIGS. 29 and 30 the needle comprises a tubular shaft 705 defining an axial flow passage 707 and a solid cylindric tip piece 709 having a hemispherical distal end and a proximal end affixed, as by laser welding, to the needle at a junction 711. The needle has a port 713 opening laterally with respect to the longitudinal axis of the needle. This port 713 may be at a location adjacent the junction 711 and is formed at an angle α relative to the longitudinal axis A of the needle. Angle α preferably corresponds to the angle θ (e.g., 15–35 degrees, and more preferably about 25 degrees) of the cannula passage 215, so that fluid discharged from the needle exits in a generally vertical direction into the reaction vessel, as discussed above. As shown in FIG. 30, the port 713 has an elongate, generally racetrack-shape, but it will be understood that other shapes may also be suitable. The port is preferably formed using an electrode discharge machine (EDM) or other suitable drilling equipment. The needle shaft 705 and tip piece 709 are preferably formed of the same material, such as 316 stainless steel. After the port 713 is formed, as by drilling, the inside surfaces of the port and the axial passage 707 at the juncture between the passage and the port are preferably polished or otherwise smoothed to eliminate any irregular surfaces which might inhibit the flow of material through the needle.

Figure 31:
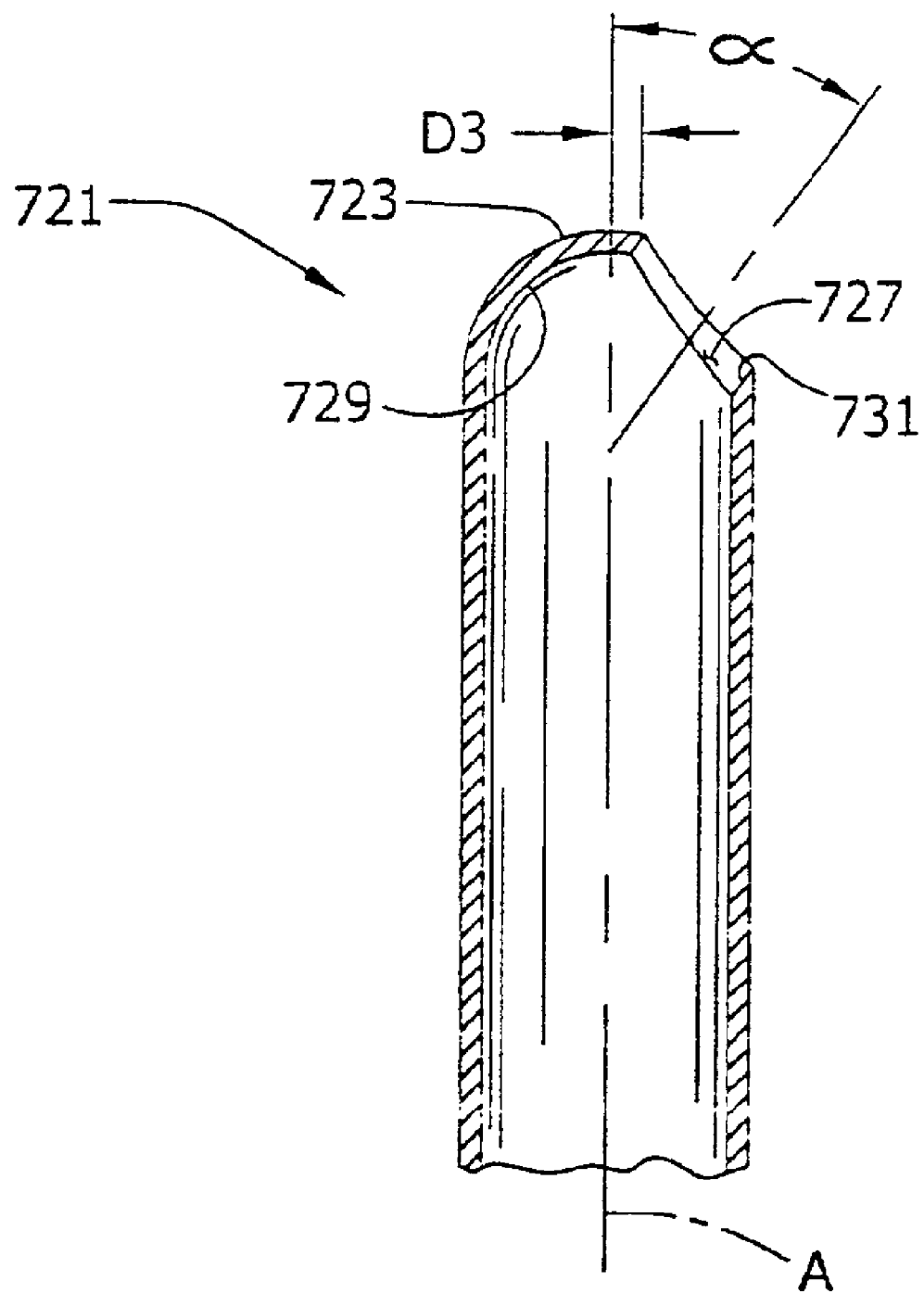
FIG. 31 is a view similar to FIG. 29 showing another needle and port configuration.

FIG. 31 shows an alternative needle design, generally designated 721, in which the needle is formed as a single piece of tubing having a distal end 723 which is only partially rounded, as indicated at 725, meaning that the curvature of the tip extends on both sides of the longitudinal axis A of the needle but not a full 180 degrees. Such a partially rounded configuration also reduces the wear on the sealing mechanism 221 compared to prior designs. As with prior embodiments, the needle 721 is formed with a laterally opening port 727 which extends at the aforementioned angle θ relative to the longitudinal axis A of the needle. The surfaces 729 defining the port 727 are smoothed (e.g., as by a polishing operation) to eliminate any sharp edges.

Other needle configurations having rounded tips and laterally opening ports may also be suitable.

The reservoir 391 and transition 411 of the cannula 21 described above generally function as an adapter for connecting the flow line 431 of larger inside dimension (e.g., 0.062 in. diameter) to the needle 401 (or 701) of smaller inside dimension (e.g., 0.0155 in. diameter). In the specific embodiments previously described, the reservoir 391 provides additional capacity for storing fluid. However, in some situations, additional capacity may not be essential, in which case the reservoir may be substantially eliminated.

In particular, FIGS. 32–37 illustrate a cannula, generally designated 801, comprising a needle 803 and an adapter in the form of a transition, generally designated 805, for connecting the flow line 431 to the needle. The transition has a generally cylindric body 807 with a flow passage 811 formed therein extending from one end of the body to the other generally along the central longitudinal axis 813 of the body. The body may be of suitable material, metal or non-metal, such as 304 stainless steel. The proximal end of the needle 803 is received in a recess (e.g., counterbore 815) in the distal end of the transition body 807 and is secured in place, as by laser welding, with the needle in closely adjacent (and preferably in contact with) an internal shoulder 817 formed by the counterbore, and with the transition and needle in substantially co-axial relation.

Figure 34:
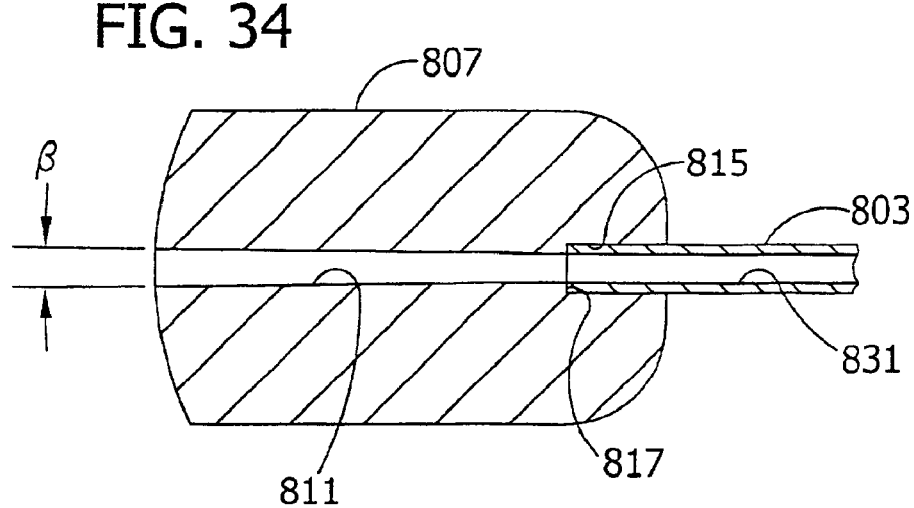
FIG. 34 is an enlarged portion of FIG. 33 showing the connection between the adapter and the needle.

In the embodiment shown, the flow passage 811 in the body 807 of the transition is tapered toward the distal end of the body, the inside dimension (e.g., circular diameter) of the passage at its distal end being substantially identical to the inside dimension (e.g., circular diameter) of the needle 803 at its proximal end (FIG. 34). The taper of the passage 811 is gradual to provide for a substantially smooth laminar flow through the passage and into the needle, so that the concentration of any particles in the fluid remains essentially uniform throughout its travel through the transition and needle. The preferred angle of taper, indicated as β in FIG. 34, is preferably in a range of 0.2–5 degrees, more preferably in a range of 1.0–3.0 degrees, and most preferably about 1.2 degrees. The tapered passage 811 may be formed in any suitable manner, such as by a conventional EDM process. The length of the transition 805 will depend on various factors, including the magnitude of the taper and the relative inside dimensions of the flow tube 311 and the needle 803. By way of example, but not limitation, the transition body 807 has a length of about 1.5–3.0 in., and preferably about 2.2 in., tapering from an inside dimension of about 0.06 in. at the proximal end of the flow passage 811 to an inside dimension of about 0.016 in. at the distal end of the flow passage where it joins the flow passage 831 of the needle. Further by way of example, the body 807 has an outside dimension of about 0.15–0.3 in., and preferably about 0.18 in.

The transition 805 has a fitting 821 at its proximal end, preferably formed as an enlarged integral part of the body 807. As shown in FIG. 33, the fitting 821 is internally threaded, as indicated at 823, to receive a compression nut 825 for securing the fluid flow line 431 to the transition 805. In the embodiment illustrated, the fitting 821 is formed with exterior wrench flats 829 (FIGS. 36 and 37) which may be used to tighten the compression nut 825 in the fitting.

Figure 35:
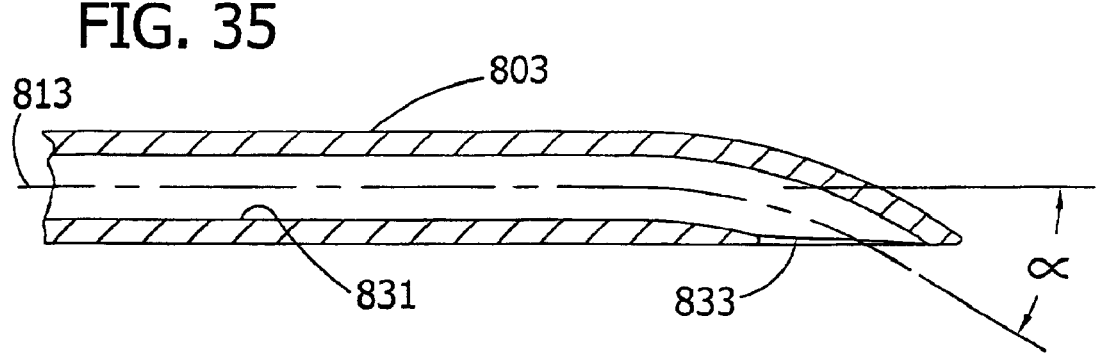
FIG. 35 is an enlarged portion of FIG. 33 showing a ported end of the needle.
Figure 36:
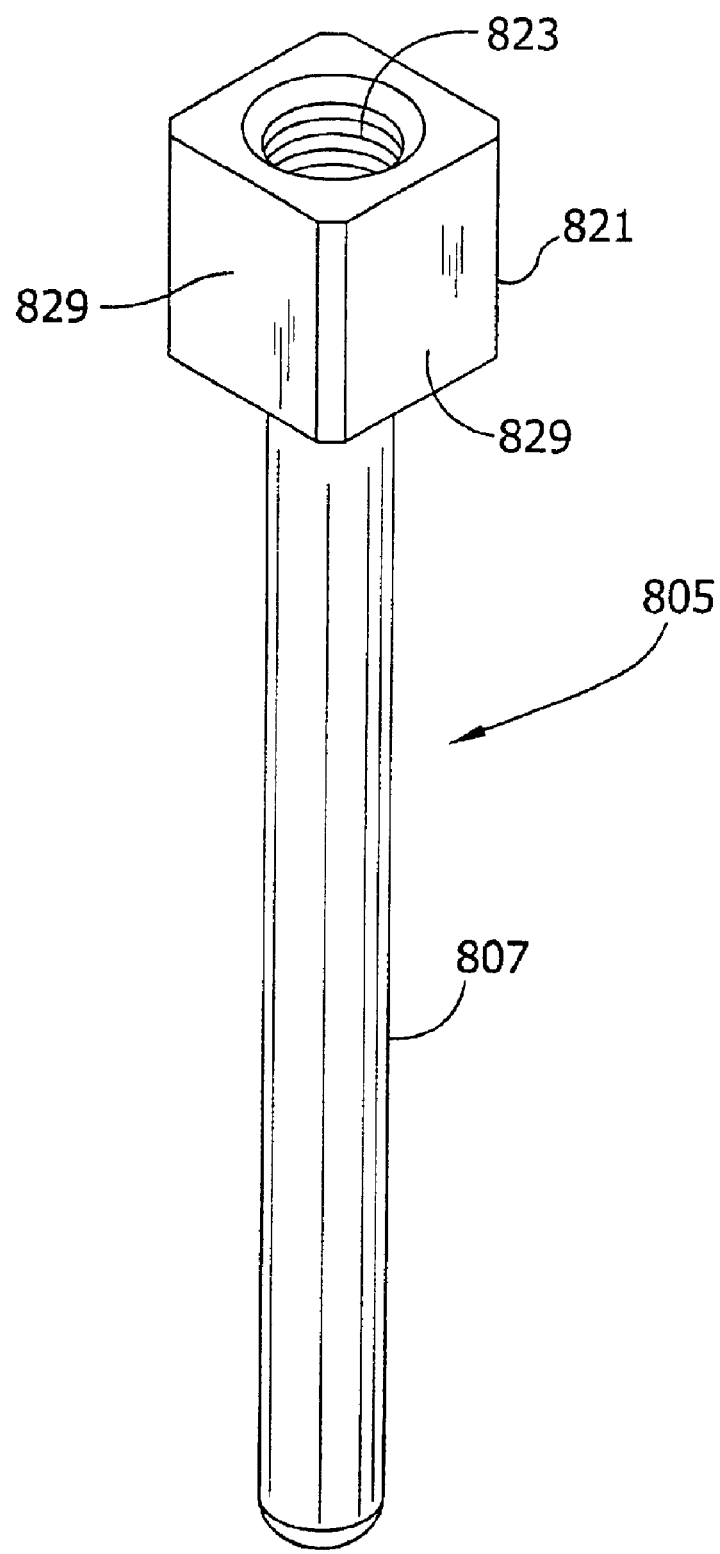
FIG. 36 is a perspective view of the adapter of FIG. 32.
Figure 37:
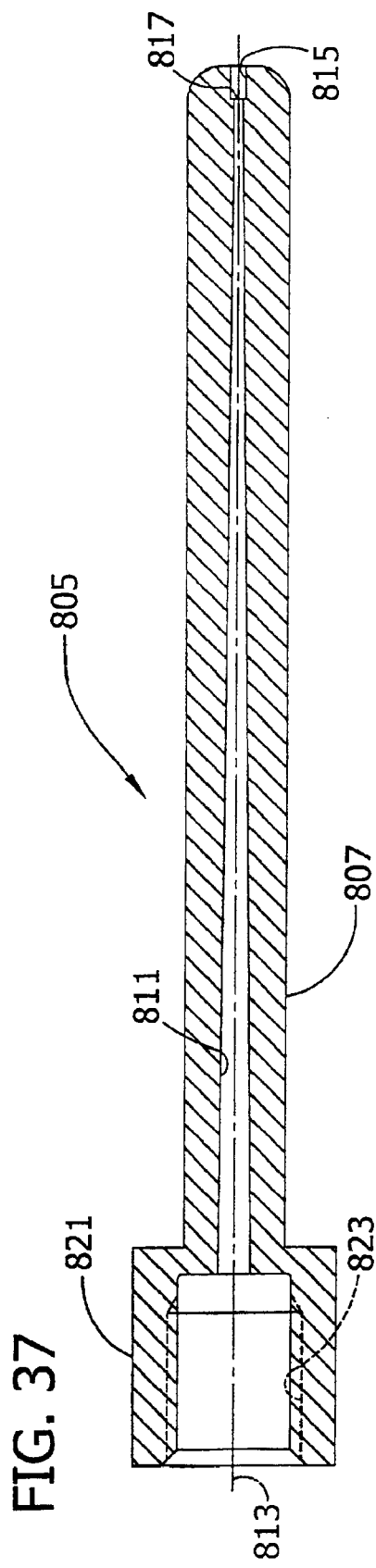
FIG. 37 is a sectional view of the adapter of FIG. 36.

Referring to FIG. 35, the needle 803 of cannula 801 has an outside dimension and an inside surface defining a flow passage 831 with a port 833 at the distal end of the needle opening laterally at an oblique angle α relative to the longitudinal axis 813 of the needle, much like the port 409 of cannula 21 described above.

In an embodiment where the cannula includes a reservoir, as shown in FIG. 23, for example, the reservoir may be formed with an integral fitting, similar to fitting 821 on transition 805, for connection of the reservoir to the fluid line 431.

The cannula 801 is particularly adapted for the transfer of solutions between the fluid line 431 and the needle 803. However, it is contemplated that the cannula may also be suitable for handling slurries.

It will be apparent from the foregoing that a cannula of the present invention, in a broad sense, comprises a needle and an adapter for connecting the needle, which has a relatively small inside dimension, to a fluid flow line having a larger inside dimension. The adapter may comprise the combination of a reservoir and a transition (e.g., FIG. 23), or a transition without a reservoir (e.g., FIG. 32). The cannula may be used for transferring fluid in a parallel reaction process, or in other applications. The volumetric capacity of the cannula (i.e., the combined volumetric capacities of the needle and whatever adapter is used) is preferably in the range of about 0.1 μl–5000 μl, more preferably in the range of about 1 μl–5000 μl, and even more preferably in the range of about 10 μl–5000 μl.

The operation of the robot system 23, the various valves for delivering gases to and from the reactor vessels, and other electronic components of the system are under the control of a suitable system processor and software (or firmware). Reference may be made to the aforementioned International Application No. PCT/US 99/18358 (International Publication No. WO 00/09255) for more detail. In general, however, the robot system 23 is operable to use the left robot arm 307L to service one bank of reactor modules 9M (e.g., the left three modules in FIGS. 1 and 2) and the right robot arm 307R to service the remaining modules (e.g., the right three modules in FIGS. 1 and 2). Using multiple robot arms to service different sections of the reactor matrix speeds set-up of the parallel reactor system and manipulation during the course of the reactions. Alternatively, the robot system could have only one arm 307 to service all modules, or three robot arms could be used. When using multiple robot arms, different arms could be dedicated to delivering different reaction materials to all or less than all of the reactor modules. The precise locations of the various components of the reactor system (e.g., cannula passage 215 entry ports, wash towers 101, 111, ultrasonic cleaners 141, vial positions in the racks 17) are programmed into the robot system in a manner which will be understood by those skilled in the art.

The general operation of the system will now be described. First, vessels and stirrers are installed and the reactor covers 195 are replaced and secured. Optionally, but preferably, a set of purge procedures is followed to purge all inlet lines, particularly those inlet lines 57 that will contain reactant gas. These purge procedures may not be necessary if the previous run left the reactor in a ready or purged state. Generally, the purging is carried out so that all lines and reactor vessels contain a desired atmosphere or gas. In the delivery or inlet lines, typically, a reactant gas may be used, such as ethylene gas, to ensure that no dead volumes or other gases are in the delivery lines.

Thereafter, liquid components are added to the reactor vessels. For example, if catalytic materials for a polymerization reaction are to be characterized, the vessels may contain a solvent or diluent and other liquid reagents (e.g., a liquid co-monomer, such as 1-octene, 1-hexene or styrene, if desired). Suitable solvents may be polar or non-polar and include toluene and hexanes. The solvents loaded into the reactor vessels may be, but are not necessarily, the same solvents used in other parts of the apparatus (e.g., the working fluid used in the syringe pumps and the solvents used in the wash towers). Thereafter, the temperature set point of the reaction is set and the temperature is allowed to stabilize. Then the reactors are charged with the atmospheric gas for the reaction, which may be an inert gas or reactant gas, in order to bring the vessels to the desired operating pressure, which is typically in the range of from 0–500 psig. If the reaction atmosphere is a reactant gas (e.g., a gaseous monomer, such as ethylene), the liquid reagents are typically allowed to become saturated with the gaseous monomer such that the reaction vessel contents reach an equilibrium point. In the example being followed (i.e., a catalyzed polymerization reaction), a catalyst particle-containing fluid or slurry is then injected into the vessels. If a catalyst is the particulate (i.e., a solid supported catalyst) then the catalyst (e.g., including co-catalysts or activators) and non-catalyst reagents (e.g., scavengers) are added to the vessels. Preferably, the catalyst in slurry form is the last component to be added to the reactor vessels.

Generally, as used herein, a slurry comprises at least two components, including (1) a solid particulate and (2) a liquid dispersing medium or diluent. The particulate is preferably a solid catalyst (e.g., a zeolite) or solid supported catalyst (e.g., an organometallic complex supported on a solid support, such as alumina or silica). Slurries of this type are known in the art. The amount of catalyst depends on the experimental design as discussed herein. Typically, the slurry contains a sufficient quantity of the liquid diluent to disperse the solid particulate in a substantially homogenous suspension with appropriate agitation as necessary. The diluent is typically not a solvent for the solid catalyst or solid supported catalyst, but may be a solvent for other reaction materials, such as monomer or scavenger. The viscosity and density of the diluent can be selected to facilitate substantial homogeneity of the slurry upon agitation. As used herein, substantially homogeneous means that the particulates are dispersed sufficiently in the diluent so that upon aspiration of a sample from the slurry, a consistent fraction of particulate is aspirated reproducibly to within scientifically acceptable error. This can be judged, e.g., on the basis of polymer productivity or catalyst efficiency. Slurry homogeneity allows for aspiration of a known volume of slurry, from which can be determined the quantity of catalyst that is being used in a particular reaction (e.g., being injected into a reaction vessel according to the design of the combinatorial or high throughput experiment). For example, 10 mg of solid supported catalyst combined with sufficient diluent to produce 1 ml of slurry can provide for a catalyst injection of 1 mg for every 100 $\mu l$ that is aspirated into a cannula 21 from a homogenous slurry. Thus, determination of catalyst to be injected (on the basis of moles or mass) can be determined on the basis of known volumes in the cannula and/or other parts of the reactor system described herein. Also, in other words, the slurry for injection can be adjusted (e.g., in terms of concentration of solid supported catalyst in the slurry) to accommodate the equipment in use (e.g., cannula volume) as well as the design of the combinatorial or high throughput experiment.

The preparation of the slurry for injection is highly dependent on the exact chemistry in practice. Generally, slurries are prepared by mixing the particulate solid material and the liquid dispersing medium or diluent and thereafter agitating, preferably swirling or vortexing, the mixture to form a substantially homogenous slurry in which the particulate solid material is suspended in the liquid. If the reactor vessels are initially charged with a liquid solvent, the same solvent may be used as the liquid dispersing medium for slurry preparation. Many factors can be adjusted to accommodate different chemistries, including the timing of adding the liquid dispersing medium to the particulate solid material to make the slurry, the ratio of the particulate solid material to diluent, the intensity with which the slurry mixture is agitated (e.g., the rate of swirling or vortexing) during preparation, the rate of cannula insertion into and out of the slurry, and the size and shape of the vial from which the slurry is aspirated prior to injection. In the case of catalytic slurries, some solid catalysts and some solid supports of supported catalysts are fragile and may degrade as a result of agitation (e.g., in terms of particle size or shape) or the time for slurry preparation may be so long that the liquid dispersing medium will evaporate, thereby changing the concentration of the catalyst in the slurry from that desired by the experimental design. Thus, in one preferred embodiment, the slurry is prepared within a limited time prior to injection, for example less than 90 minutes prior to injection, more preferably not more than 45 minutes prior to injection, more preferably not more than 10 minutes prior to injection, still more preferably not more than 5 minutes prior to injection and especially not more than 1 minute prior to injection. Depending on the speed set for the robots, etc., slurry may be prepared by mixing the particulate solid material and the liquid dispersing medium within about 30 seconds prior to injection to the reactor vessel, as described herein. Other factors that can be adjusted include the intensity of agitation of the slurry mixture. The rate of swirling or vortexing of the slurry necessary to achieve a substantially homogeneous slurry depends on the concentration of the particulate solid material in the liquid dispersing medium and the volume and shape of the mixing vial. In general, the higher the concentration of solid particles in the slurry, then the higher the vortexing rate necessary to ensure a substantially homogeneous slurry. Similarly, the lower the concentration of solid particles in the slurry, the lower the vortexing rate should be. Examples of suitable slurry vortexing rates include from about 100 rpm to about 1300 rpm. Mixing vial sizes include 20 ml, 8 ml, and 1 ml.

For a catalytic reaction in which the catalyst is on a solid support, in order to prepare the slurry, the solid supported catalyst is first weighed, with the weight being used to calculate the amount of liquid dispersion medium that is added to the supported catalyst to prepare the slurry for injection. The preparation of the slurry for injection can be important with respect to the size of the cannula, since the cannula can accommodate only a limited amount of slurry. Thus, it is important to calculate the concentration of the slurry, the desired catalyst amount on the support (e.g., silica) and then the desired amount of liquid dispersing medium.

To initiate a typical run of reactions, the orbital shakers 13 are actuated to shake the racks 17 containing the vials and agitate the slurry materials contained therein to provide a substantially homogeneous slurry. The robot system is then actuated to move the cannulas to fluid transfer locations in which the desired quantities of slurry material are aspirated from vials in respective racks on the shakers, the left cannula 21 (as viewed in FIG. 1) aspirating from one or more vials in the left rack 17 and the right cannula 21 aspirating from one or more vials in the right rack 17. During aspiration, the cannulas are preferably in a vertical position and the shakers are preferably in operation to agitate the slurry and ensure that the slurry aspirated into the cannula is substantially homogenous. When the cannula 21 is entering the vortexing slurry, the cannula speed along the Z axis of the robot is slowed down so that the cannula entering the vortexing slurry does not substantially disturb the homogeneous slurry. The cannula is preferably paused from about 1–2 sec. in the vortexing slurry prior to aspiration in order to ensure that a substantially homogeneous slurry is aspirated into the cannula. Also, prior to aspiration, the speed of aspiration is slowed (e.g., by slowing the aspiration rate of the syringe pump 43) to avoid particle selectivity or other issues that might impact the homogeneity of the slurry that is aspirated into the cannula. Thereafter, the desired volume of slurry is aspirated into the cannula.

In the preferred embodiment, after aspiration (transfer) of an appropriate quantity of slurry into a cannula 21 is complete, the robot system 23 moves the cannula to aspirate a small volume of barrier liquid (e.g., 30–50 $\mu l$ of optionally the same liquid charged to the reactor vessels) into the tip of the needle 401. The robot system is then operated to lift the cannula along the Z-axis of the respective robot arm 307L, 307R to a height sufficient to clear the reactor modules 9M; the power actuator 329 is operated to rotate the robot arm on its R-axis to tilt the cannula to its fluid-delivery angle (e.g., 25°); and the cannula is moved along X and/or Y-axes to a position in which the needle is ready for insertion into the cannula passage 215 leading to the first vessel to be loaded with slurry, as shown in FIG. 12. The cannula is held in this position for a short dwell period (e.g., 1–2 seconds) sufficient to allow any vibratory or harmonic movement of the needle to cease, following which the angled cannula is moved along the Z axis of the elongate rack 311 to cause the needle 401 to penetrate the wiper member 265 to wipe any slurry material off the outside of the needle. The needle continues to advance into the entry port of the cannula passage 215 and through the annular seal 229 to a position (FIG. 13) immediately upstream of the duckbill valve lips 241, where the advance of the needle 401 is paused while the robot is signaled to increase the speed of the needle 401 along the Z-axis of the rack 311. The syringe flow rate is also increased. Alternatively, the syringe flow could be increased after the liquid barrier has been aspirated. In either event, after a dwell in the position of FIG. 13, the needle is pushed forward at a relatively high speed through the valve, forcing the lips 241 of the duckbill valve apart, and down through the passage 215 to the fluid delivery or dispensing position at the fluid transfer location shown in FIGS. 10 and 14. As the needle approaches its dispensing position, the head 455 of the cannula support 443 engages the wiper member frame 263 and remains in that position as the needle continues to advance to the position shown in FIG. 10 where the distal end of the needle 401 is disposed inside the vial 165 at a level above the contents of the vial, and the port 409 in the needle faces generally downward. The high speed of the needle 401 in combination with the small volume of barrier liquid in the tip of the needle and high syringe flow rate helps to avoid possible reaction from occurring in the cannula (e.g., in an embodiment where the slurry comprises a catalyst).

With the needle 401 in its FIG. 10 delivery or dispensing position, solvent is pumped into the cannula 21 through the solvent line 431 to force the small volume of barrier liquid and the predetermined quantity of slurry material from the cannula directly into the vial 165. A predetermined quantity of chaser solvent is also dispensed in an amount sufficient to ensure that the slurry is effectively transferred to the vessel. Preferably, slurry preparation and the speed with which the robot system manipulates the cannula are controlled such that the slurry delivered to the vial remains substantially homogenous. In an especially preferred embodiment, the slurry is prepared less than 90 minutes before delivery to the first reaction vessel (vial 165) and the slurry is delivered to the vial within 60 seconds of aspirating the slurry into the cannula.

Because the contents of the vessel are already under pressure, the slurry material must be delivered from the cannula at a pressure greater than the vessel pressure. Typical reaction pressures vary from about ambient to 500 psig, and more preferably from about 50–300 psig, so at least some of the syringe pumps 43 (e.g., pumps 43a) should have the capability of generating a delivery pressure of up to 500 psig or greater. Since the port 409 at the distal end of the needle 401 is facing down, the slurry preferably does not contact or accumulate on the side walls of the vial 165 but rather is deposited on the surface of the contents in the bottom of the vial where it can be properly mixed. Following delivery of the slurry material to the vial, the robot is operable to withdraw the distal end of the needle 401 at high speed past the lips 241 of the duckbill valve to the position shown in FIG. 13 between the lips 241 and the seal 229. The needle is held in this position for a short dwell period (e.g., 1–2 seconds) sufficient to enable the lips 241 of the valve to close and for the robot speed along the Z-axis of the rack to be reduced to a slower speed (i.e., the robot arm speed along the Z-axis is reset at this point to normal). During this time the annular seal 229 is in sealing engagement with the needle 401 to prevent any substantial leakage past the lips while they are closing. The robot then moves the needle at the slower speed to a position where it is completely withdrawn from the cannula passage and the cannula is again at a height sufficient to clear the reactor modules. As the needle 401 withdraws from the cannula passage 215, the head 455 of the cannula support 443 returns to its needle supporting position shown in solid lines in FIG. 26.

After each aspiration into the cannula 21 and after each delivery from the cannula, the cannula is preferably moved to the cleaning apparatus 25 and cleaned for several reasons. First, cleaning avoids cross-contamination of materials. Second, small particles (e.g., silica particles) which might otherwise interfere with or damage the reaction equipment are removed. And third, cleaning removes any build-up of polymer material on the needle 401 adjacent the port 409. (Some polymerization may occur in the needle prior to dispensing, when the needle is first exposed to reactant gas in the cannula passage.) If such build-up is not removed, it could interfere with the delivery of material from the cannula and subsequent aspirations into the needle. Prior to insertion of a cannula into the appropriate wash tower 101, 111 and/or ultrasonic cleaning device 141, the power cylinder 329 of a respective robot is actuated to rotate the robot arm 307L, 307R to its home (or non-tilted) position in which the needle is vertical. The needle is then lowered for cleaning.

The robot system 23 is operated to move the cannula 21 back to the rack 17 containing the slurry source followed by aspiration and delivery of slurry to a second and subsequent vessels as necessary to load the reactor. Although the same slurry can be delivered to each of the vessels, it may be desired in some reaction protocols to deliver a second slurry that differs in composition from the first slurry to at least some of the remaining vessels in the reactor. The second slurry may differ in composition in terms of solid particulate concentration and/or the solid and liquid components of the slurry. For a single run of the reactor, there can be as many slurries as there are reaction vessels such that there may be 1, 2, 8, 16, 24 or 48 of different slurry compositions.

It will be understood that the two robot arms 307L, 307R move independent of one another to carry out the dispensing process in the most efficient manner. As noted previously, the left robot arm typically services the left bank of reactor modules and the right arm the right bank of modules. Alternatively, one robot arm could be used to service all reactors. The speed at which the robots move the cannulas may also vary to reduce the time needed to load the vessels. For example, the cannula 21 may be moved at higher speeds when larger distances are being traversed, and at slower speeds at other times, as when the cannula is approaching various destinations and during the initial stages of needle insertion into a cannula passage 215.

After the vessels have been loaded, the reactions are monitored for a desired interval of time or reaction stage or until the reactions are considered to be finished, following which quenching gas (e.g., $CO_2$) is delivered to the vessels through lines 57 to terminate the reaction. After the reaction is completed, and prior to removing samples and vessels, appropriate venting procedures should be followed to ensure that there is no loss of product through the vent lines. Specifically, if venting of the reaction vessels is too fast, the solid supported catalyst or other particulate materials (e.g., such as polymer particles) may vent through the vent lines 57. Venting procedures may include slow venting (e.g., vent valve cycling) and/or inert gas purging (e.g., argon or nitrogen). After the appropriate venting procedures are complete, the reactor covers 195 are removed to allow removal of the reaction samples and replacement of the removable vials and stirrers 175.

In a preferred embodiment, the reaction vials 165 used in the reactor modules 9M should have a cross-sectional shape corresponding to the cross-sectional shape of the wells 163 (e.g., circular), a volume somewhat greater than the total volume of reaction materials and/or products to be contained by a vessel, and a height such that when the vial is placed in a well 163, the rim of the vial is at an elevation below where the cannula passage 215 enters the well. Preferably, the open upper end of the reaction vial is positioned for receiving the distal end of the needle 401 in its delivery or dispensing position, with the port 409 of the needle located inside the vial at an elevation below the upper end of the vial and facing downward. Thus, the height of the vial will vary depending on various factors, including the angle of the cannula passage 215, the reactor height, the depth of the well 163, and other factors. In the preferred embodiment, the vial has a rounded bottom and a cylindric side wall extending up from the bottom and terminating in a rim defining an open upper end of the vessel. For use in a reactor block of the type shown in FIG. 10, the side wall of the reaction vial has an inside diameter in the range of about 0.5–2.5 in., more preferably in the range of about 0.5–0.75 in., and most preferably about 0.609 in.; the vial has an overall height in the range of about 1.0–4.0 in., more preferably in the range of about 1.5–3.0 in., and most preferably about 2.15 in; and the vial defines a volume in the range of about 5–200 ml, and preferably in the range of about 5–20 ml, and most preferably about 10 ml.

In the event there is a need or desire to move, remove, and/or replace one or more of the reactor modules 9M, as during a maintenance procedure, the carriage extension 83 is disconnected from the fixture 85 on the table 3 by disconnecting the master locking device 81. This disconnection triggers a shut-off switch which renders the robot system 23 inoperable. Disconnection of device 81 allows all of the carriage plates 67 to be moved together as a unit along the rails 61. If desired, one or more of the other carriage plate locking devices 75 may be released to disconnect the appropriate carriage plates 67 from one another to allow the plates to be slidably moved relative to one another along the rails 61 and the reactor modules 9M to be separated for convenient service or rearrangement of the reactor matrix. After the modules are serviced and/or rearranged, the carriage plates 67 are reconnected and the carriage extension 83 reconnected to the table fixture 85 to render the robot operable.

It will be observed from the foregoing that the parallel reactor apparatus of the present invention represents an advance over prior systems. The system can be used to deliver hard-to-handle (e.g., "sticky") slurry materials. For example, as discussed herein, solid supported catalyst particle size may be so small as to be considered "catalyst fines" or other characterizations that are typically used in industry. At these particle sizes, reactor or equipment fouling is possible. One of the benefits of this invention is that such fouling is minimized while still providing for the delivery of accurate volumes to the reactor vessels in an efficient, fully automated manner, and at pressures other than ambient, if desired.

The present invention may also be used to monitor and/or control ongoing chemical processes of virtually any type or scale, and in some embodiments, offers the capabilities or real time or near real time process monitoring and/or control. For example, the robotic system 23 can be used to transport a cannula (e.g., 21, 801) to a fluid transfer location to aspirate a fluid sample from a chemical reactor, a chemical reaction process line or a sample line in fluid communication, optionally isolatable fluid communication, with such a reactor or reaction process line, and then to transport the sample, either with or without intermediate treatment, to a sample analyzing device, such as a liquid chromatography instrument. The sample can be transferred to the analyzing device in any suitable fashion, including but not limited to insertion of the cannula (e.g., a needle portion thereof) into an angled cannula passage, preferably in some embodiments containing an appropriate sealing mechanism allowing for transfer of the sample at pressures other than ambient (including, for example, at pressures disclosed herein). If a sealing mechanism is used, it can take carious forms, such as a simple septum, or the combination valve/seal 227, 229 described above. In any event, based on the analysis of the sample by the analyzer, various parameters of the ongoing process can be monitored and/or controlled, as needed or desired. Moreover, in some embodiments, the fluid transfer procedure and analysis can be accomplished in a short period of time (relative to the kinetics of the reaction parameter of interest), so that any necessary changes to the process can be implemented quickly—thereby allowing for real time or near-real time monitoring and/or control of the chemical reaction. Exemplary rapid analysis techniques for characterizing polymerization product mixtures are disclosed in U.S. Pat. Nos. 6,175,409, 6,260,407, 6,265,226, each of which is hereby incorporated by reference with respect to such techniques. As another example for using the robotic fluid transport system of the present invention, the robotic system 23 can be used to transport a cannula (e.g., 21, 801) to a fluid transfer location to deliver a fluid sample to a chemical reactor, a chemical reaction process line, or a feed line in fluid communication, optionally isolatable fluid communication with such a reactor or reaction process line. In any case, the chemical process can be of any scale, i.e., production (i.e., commercial) scale, pilot plant scale or research scale (e.g., traditional bench scale or combinatorial scale), and the amount of fluid transferred will vary accordingly. Generally speaking, the volume of fluid transfer will be in the range of about 0.1 $\mu$l–5000 $\mu$l, more preferably about 1 $\mu$l–5000 $\mu$l, more preferably about 10 $\mu$l–5000 $\mu$l, more preferably about 1 ml–500 ml, still more preferably about 1 ml–100 ml, yet more preferably about 2 ml–25 ml, and most preferably about 5 ml–15 ml. For chemical reaction processes, the chemical reactor or chemical reaction line can be a stand-alone reactor, or can be one or more reactors integrated into a larger reaction scheme, and can generally be a batch reactor, a continuous flow reactor or a semi-continuous reactor, in each case with various other configuration details known presently or later-developed in the art of chemical reactor design.

The following example is simply intended to further illustrate and explain the present invention. This invention, therefore, should not be limited to any of the details in this example.

EXAMPLE

In general, with the reactor modules 9M in a benign state, and the reactor covers 195 removed, reaction vials 165 are inserted in the reactor wells 163. Disposable stirrers 175 are attached to the drivers 179 and checked to ensure that the coupling 181 is engaged. Before the covers 195 are re-secured, a metal tool is used to push each vial all the way to the bottom of the reactor well 163, ensuring the vial is not obstructing the cannula passage 215. After the vials are verified to be in the correct position, the reactor covers 195 are secured to the reactor modules. Purge routines are run as defined earlier.

Experimental library design is supplied, which specifies reactant components, quantities as well as database storage and retrieval parameters. For a standard catalyzed polymerization reaction, the robot system 23 is instructed to add to each reaction vial 165 200 µl of liquid co-monomer 1-octene, followed by 4500 µl of hexane solvent, with the left arm 307L of the robot servicing the left 3 modules 9M of the reactor and the right arm 307R of the robot system servicing the right 3 modules of the reactor (see FIG. 1). While adding solvent and co-monomer, syringe flow rates are set to initial values of:
Start Speed: 100 µl/s
Top Speed: 300 µl/s
Cutoff Speed: 100 µl/s
For each X,Y and Z movement, there are 3 speeds for each robot arm 307 and, in this experiment, those speeds are the same for the right and left arms of the robot system. These speeds are set to have the following initial values:
Start speed: X=11.17 mm/sec, Y=28.11 mm/sec., and Z=9.8 mm/sec.
End speed: X=893.6 mm/sec, Y=568.8 mm/sec., and Z=196 mm/sec.
Acceleration: X=900 mm/sec$^2$, Y=800 mm/sec$^2$, and Z=500 mm/sec$^2$.

Once these reagents are added, the temperature is set to the specified temperature from the experimental design, which in this case is 85° C. Simultaneously, the stirrers 175 are activated to stir at their desired RPM, which is 800 RPM. The temperatures in the reaction chambers of the reactor modules 9M are allowed to stabilize to their set point(s). Upon stabilization, each reaction chamber is charged with ethylene gas at a pressure of about 100 psig, with the uptake of ethylene being monitored. After saturation of the solvent with ethylene (which takes an average of about 10 minutes), non-catalyst and catalyst material can be added to each reaction chamber. For example, 200 µl of MMAO (modified methylamumoxane) can be added as a scavenger, followed by 500 µl of additional hexane solvent acting as a chaser to flush the cannula 21. (Note that this entire process is automated with the robot system 23). During aspiration of the MMAO and hexane, the initial syringe flow rates are used. During movements between the reactor modules and reagents, the stated initial robot arm speeds are used. Once the cannula 21 has reached the position shown in FIG. 12, the arm speed is slowed down to have a Z acceleration component of 250 mm/sec$^2$, allowing the needle 401 to pierce the wiper member 265. This arm speed is used throughout this portion of the addition sequence. When the cannula reaches the fluid delivery the position shown in FIG. 14, the syringe flow rate is changed to 100 µl/s (start), 400 µl/s (stop), 100 µl/s (cutoff). After the cannula is removed from the cannula passage 215, the robot arm speeds and syringe flow rates are reset to their initial values. The cannula 21 is then cleaned at the appropriate wash stations 101, 111 and flushes a sufficient volume of solvent to remove any and all memory of the previous reagent, on average 1000 µl per wash station.

Preparation of a slurry is initiated by adding a solid supported catalyst to each reaction vial 165. The solid supported catalyst is prepared as is well known in the art, as disclosed for example in U.S. Pat. No. 5,643,847 or U.S. Pat. No. 5,712,352, each of which is incorporated herein by reference. After the above described wash sequence has concluded, the two robot arms 307L, 307R move at the same speed to move the cannulas 21 to their respective orbital shakers 141. Each shaker supports a rack 17 comprising two rack panels each holding 24 individual 1.0 ml mixing vials, spaced in an 8×3 array, 48 vials total. Of the 48 mixing vials 24 contain a solid supported catalyst e.g., 10 mg of solid supported catalyst to be delivered to corresponding reactor vials 165. The shaker is operated at a speed of 1100 RPM. The cannula 21 aspirates diluent from a separate reagent vial accessible to the robot system 21, following which the cannula is moved to the first mixing vial where it dispenses 500 µl of diluent, in this case toluene. The cannula 21 is then washed at a station 101, 111 for a sufficient period of time, during which the solid supported catalyst particles in the mixing vial 165 are suspended in the diluent to provide a substantially homogeneous slurry. After washing, the cannula moves back to a position just above the rim of the mixing vial 15 containing the slurry for the first reaction vial 165 and pauses. This pause allows the robot arm speed and the syringe flow rate to be decreased to the initial values noted above, except the Z-deceleration component is set to 250 mm/sec$^2$ and the syringe flow is changed to 50 µl/sec (start), 25 µl/sec (stop) and 50 µl/sec (cutoff). As described, the lower speed allows the cannula to enter the slurry without altering the vortexing and allows aspiration of substantially homogeneous slurry without selectivity. While the cannula is paused above the rim of the mixing vial, the syringe pump is filled with 500 µl of a chaser solvent (toluene) from the same solvent reservoir. The cannula then descends into the slurry and pauses. 100 µl of slurry containing 1 mg of solid supported catalyst is aspirated from the first mixing vial 15. The robot arm speed and syringe flow rate are reset and the cannula 21 is moved to a vial on the same rack 17 containing solvent and aspirates 50 µl of solvent to act as a liquid barrier. The cannula is then moved to the reactor module containing the first reaction vial 165, and the injection sequence described earlier and shown in FIGS. 12–14 is carried out. Prior to movement of the cannula from the position shown in FIG. 13 to the delivery position shown in FIG. 14, the speed of the robot arm is increased to have a Z-acceleration component of 1450 mm/sec$^2$. This allows the cannula 21 to reach fluid delivery position as quickly as possible. The syringe flow rate is also increased to 100 µl/sec (start), 400 µl/sec (stop), 100 µl/sec (cutoff). Upon reaching the delivery position, the syringe pump 43 forces the entire contents of the cannula, i.e., solvent chaser, slurry, and liquid barrier, at the highest possible flow rate. Once delivery is completed, the cannula is withdrawn from the cannula passage 215 in the manner previously described, the cannula moving first to the dwell position shown in FIG. 13, where the robot arm speed and syringe flow rate are decreased to their initial values, and then withdrawn completely from the cannula passage 215. The cannula then goes through the appropriate wash routine. The sequence is repeated for each and all reaction vials 165. Upon catalyst injection to each reaction vial, polymerization occurs, allowing catalyst performance from a slurry to be evaluated.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A method of transferring fluids using a cannula, comprising connecting the cannula to a robot transport system, operating the robot transport system to transport the cannula to a fluid transfer location, said transport involving moving said cannula along x, y and z axes, rotating the cannula to an angular orientation off vertical, and inserting the cannula while in said angled orientation into an angled cannula passage, and effecting transfer of said fluid while said cannula is in said angled cannula passage.

2. A method as set forth in claim 1 wherein the cannula is sized for holding 10 $\mu$l–5000 $\mu$l of fluid.

3. A method as set forth in claim 1 further comprising advancing the cannula through a sealing mechanism in said cannula passage before effecting transfer of said fluid to prevent the leakage of fluid from the passage.

4. A method as set forth in claim 1 wherein said fluid transfer is effected at a pressure other than ambient pressure.

5. A method as set forth in claim 1 wherein said fluid transfer is effected at a pressure of at least about 15 psig.

6. A method as set forth in claim 1 wherein said fluid transfer is effected at a pressure of about 50–500 psig.

7. A method as set forth in claim 1 wherein said cannula passage is in fluid communication with a reaction vessel contained in a reactor.

8. A method as set forth in claim 1 further comprising aspirating a sample of fluid material into said cannula at said fluid transfer location, operating said robot transfer system to transport said cannula to a sample analyzing device, and effecting transfer of fluid from the cannula to said sample analyzing device.

9. A method as set forth in claim 8 further comprising aspirating said fluid sample from a reactor vessel containing fluid reaction materials.

10. A method as set forth in claim 1 wherein the amount of fluid transferred is from about 5 $\mu$l–500 ml.

11. A method as set forth in claim 1 wherein the amount of fluid transferred is from about 1 ml–500 ml.

12. A method as set forth in claim 1 wherein the amount of fluid transferred is from about 2 ml–25 ml.

* * * * *